(12) United States Patent
Puthigae et al.

(10) Patent No.: US 8,669,108 B2
(45) Date of Patent: Mar. 11, 2014

(54) GENE EXPRESSION CONTROL IN PLANTS

(75) Inventors: Sathish Puthigae, Auckland (NZ); Jonathan Robert Phillips, Chesterfield, MO (US); Nimali Piyushika Withana, Carlton (AU); Claudia Jeannette Smith-Espinoza, Chesterfield, MO (US); Catherine Jane Bryant, Auckland (NZ); Kerry Robert Templeton, Auckland (NZ); Shivendra Bajaj, Auckland (NZ)

(73) Assignee: Vialactia Biosciences (NZ) Limited, Auckland (NZ)

( * ) Notice: Subject to any disclaimer, the term of this patent is extended or adjusted under 35 U.S.C. 154(b) by 359 days.

(21) Appl. No.: 12/935,952

(22) PCT Filed: Mar. 30, 2009

(86) PCT No.: PCT/NZ2009/000047
§ 371 (c)(1),
(2), (4) Date: Apr. 4, 2011

(87) PCT Pub. No.: WO2009/123479
PCT Pub. Date: Oct. 8, 2009

(65) Prior Publication Data
US 2011/0179517 A1 Jul. 21, 2011

Related U.S. Application Data

(60) Provisional application No. 61/042,038, filed on Apr. 3, 2008.

(51) Int. Cl.
C12N 5/04 (2006.01)
A01H 5/00 (2006.01)
C12N 15/87 (2006.01)
A01H 1/00 (2006.01)
C07H 21/02 (2006.01)

(52) U.S. Cl.
USPC .......... 435/419; 435/468; 800/278; 800/287; 800/298; 536/24.1

(58) Field of Classification Search
None
See application file for complete search history.

(56) References Cited

U.S. PATENT DOCUMENTS

| | | | |
|---|---|---|---|
| 4,795,855 | A | 1/1989 | Fillatti et al. |
| 5,004,863 | A | 4/1991 | Umbeck |

(Continued)

FOREIGN PATENT DOCUMENTS

| | | |
|---|---|---|
| WO | 01/04285 | 1/2001 |
| WO | 02/00894 | 3/2002 |
| WO | 02/50294 | 6/2002 |
| WO | 2004/058963 | 7/2004 |
| WO | 2005/123919 | 12/2005 |
| WO | 2007/049275 | 5/2007 |
| WO | 2007/078286 | 7/2007 |
| WO | 2008/121008 | 10/2008 |

OTHER PUBLICATIONS

Mian et al., BMC Plant Biol 8:27 (2008).*

(Continued)

*Primary Examiner* — Joe Zhou
*Assistant Examiner* — Russell Boggs
(74) *Attorney, Agent, or Firm* — Lathrop & Gage LLP

(57) ABSTRACT

The invention provides the isolated promoter polynucleotide sequence of SEQ ID NO:1, and fragments and variants thereof. The invention also provides constructs, plant cells and plants genetically modified to contain the promoter polynucleotide. The invention also provides methods for producing plants with altered gene expression and traits via genetic transformation of plants with the promoter polynucleotides.

16 Claims, 10 Drawing Sheets

```
caagagacaaaattgccgggattcatttcgagtagcgacacttgacgagaacattttttttgcttt
tccagagaacccacgaaaaggccgggaagaaaagggtacaactcaaactttcgtgttccaggac
ggtatcagcatcggcggctcagccaatcacgagctttggcaagaaatgtcgacggaagaaaatgg
cagaaatttgtcgccgtcgtaccccctccctgctagcctgtcgaccgccgattcgccgtcgcgcc
cacttgcgccggtcgcgcgaacctcagccacactctcaccaacccaaaccccctgcgctagctgca
cccggctccggcatccagaagcttccggcccggggccggccggccggccacgaacgcgccgcgcgg
cctagaacattcggtcccctctcccgaccagtcgcgctctgcctgtccgcaggagtatttatta
gcgagcaccggccattttcccgCggaaggaaacgagccgcgacgctggtcttgcattcttgtgatt
acccgcgctggattcttccgtttccaagagcgattcctcgatcggagcagagttcctctgggataa
ttgctggttggttgctgctcccggctacacgaagatcctatcgtcgccttcggtttgattgatccg
tcca
```

(56) References Cited

U.S. PATENT DOCUMENTS

| | | | |
|---|---|---|---|
| 5,159,135 | A | 10/1992 | Umbeck |
| 5,177,010 | A | 1/1993 | Goldman et al. |
| 5,187,073 | A | 2/1993 | Goldman et al. |
| 5,188,958 | A | 2/1993 | Moloney et al. |
| 5,352,605 | A | 10/1994 | Fraley et al. |
| 5,364,780 | A | 11/1994 | Hershey et al. |
| 5,416,011 | A | 5/1995 | Hinchee et al. |
| 5,463,174 | A | 10/1995 | Moloney et al. |
| 5,510,474 | A | 4/1996 | Quail et al. |
| 5,563,055 | A | 10/1996 | Townsend et al. |
| 5,569,834 | A | 10/1996 | Hinchee et al. |
| 5,591,616 | A | 1/1997 | Hiei et al. |
| 5,750,871 | A | 5/1998 | Moloney et al. |
| 5,792,935 | A | 8/1998 | Arntzen et al. |
| 5,824,877 | A | 10/1998 | Hinchee et al. |
| 5,846,797 | A | 12/1998 | Strickland |
| 5,952,543 | A | 9/1999 | Firoozabady et al. |
| 5,968,830 | A | 10/1999 | Dan et al. |
| 5,981,840 | A | 11/1999 | Zhao et al. |
| 6,020,539 | A | 2/2000 | Goldman et al. |
| 6,037,522 | A | 3/2000 | Dong et al. |
| 6,074,877 | A | 6/2000 | D'Halluin et al. |
| 2004/0034888 | A1 | 2/2004 | Liu et al. |
| 2004/0123343 | A1 | 6/2004 | La Rosa et al. |
| 2004/0172684 | A1 | 9/2004 | Kovalic et al. |
| 2004/0214272 | A1* | 10/2004 | La Rosa et al. .......... 435/69.1 |
| 2006/0123505 | A1 | 6/2006 | Kikuchi et al. |
| 2007/0020621 | A1 | 1/2007 | Boukharov et al. |
| 2007/0044171 | A1 | 2/2007 | Kovalic et al. |
| 2007/0067865 | A1 | 3/2007 | Kovalic et al. |
| 2010/0242134 | A1 | 9/2010 | Puthigae et al. |
| 2010/0293664 | A1 | 11/2010 | Puthigae et al. |
| 2011/0185452 | A1 | 7/2011 | Puthigae et al. |
| 2011/0209250 | A1 | 8/2011 | Puthigae et al. |

OTHER PUBLICATIONS

Donald, EMBO J 9:1717-26 (1990).*
Kim et al., Plant Mol Biol 24:105-17 (1994).*
Dolferus et al., Plant Physiol 105:1075-87 (1994).*
Komarnytsky and Borisjuk, Genetic Engin 25:113-41 (2003).*
Jiao et al., Nat Reviews Genet 8:217-30 (2007).*
Birch, R.G. (1997) "Plant Transformation: Problems and Strategies for Practical Application," Ann Rev Plant Phys Plant Mol Biol, 48:297-326.
Bowie et al. (1990) "Deciphering the Message in Protein Sequences: Tolerance to Amino Acid Substitutions," Science 247:1306-1310.
Falquet et al. (2002) "The PROSITE database, its status in 2002," Nucleic Acids Res. 30(1):235-238.
Frohman, M.A. (1993) "Rapid Amplification of complementary DNA Ends for Generation of full-length Complementary DNAs: Thermal RACE," Methods Enzymol. 218:340-356.
Gruber et al. (1993) "Vectors for Plant Transformation," Methods in Plant Mol. Biol. and Biotech, pp. 89-119, CRC Press.
Hofmann et al. (1999) "The PROSITE database, its status in 1999," Nucleic Acids Res. 27(1):215-219.
Horsch et al. (1985) "A Simple and General Method for transferring Genes into Plants," Science 227:1229-1231.
Huang, X. (1994) "On Global Sequence Alignment," Comp. Apps in the Biosciences 10(3):227-235.
Jones et al. (1998) "The effect of chimeric transgene architecture on co-ordinated gene silencing," Planta 204:499-505.
Kumar et al., 1996 "Potato plants expressing antisense and sense S-adenosylmethionine decarboxylase (SAMDC) transgenes show altered levels of polyamines and ethylene: antisense plants display abnormal phenotypes," Plant J. 9(2):147-158.
Llave et al. (2002) "Cleavage of *Scarecrow-like* mRNA Targets Directed by a Class of *Arabidopsis* miRNA," Science 297:2053-2056.
McIntyre et al. (1996) "Strategies for the suppression of peroxidase gene expression in tobacco. I. Designing efficient ribozymes," Transgenic Res. 5:257-262.
Nielsen et al. (1991) "Sequence-Selective Recognition of DNA by Strand Displacement with a Thymine-Substituted Polyamide," Science 254:1497-1500.
Schrott, M. (1995) "Selectable Marker and Reporter Genes," Gene Transfer to Plants, Potrykus T., Spangenbert. Eds., Springer Verlag. Berline, pp. 325-336.
Triglia et al. (1988) "A procedure for in vitro amplification of DNA segments that lie outside the boundaries of known sequences," Nucleic Acids Res. 16(16):8186.

* cited by examiner

Figure 1

```
caagagacaaaattgccgggattcatttcgagtagcgacacttgacgagaacattttttttgcttt
tccagagaacccacgaaaaaggccgggaagaaaaagggtacaactcaaactttcgtgttccaggac
ggtatcagcatcggcggctcagccaatcacgagctttggcaagaaatgtcgacggaagaaaaatgg
cagaaatttgtcgccgtcgtaccccctccctgctagcctgtcgaccgccgattcgccgtcgcgcc
cacttgcgccggtcgcgcgaacctcagccacactctcaccaacccaaaccccctgcgctagctgca
cccggctccggcatccagaagcttccggccgggggccggccggccggccacgaacgcgccgcgcgg
cctagaacattcggtccccctctcccgaccagtcgcgctctgcctgtccgcagggagtatttatta
gcgagcaccggccatttttcccgCggaaggaaacgagccgcgacgctggtcttgcattcttgtgatt
acccgcgctggattcttccgtttccaagagcgattcctcgatcggagcagagttcctctgggataa
ttgctggttggttgctgctcccggctacacgaagatcctatcgtcgccttcggtttgattgatccg
tcca
```

Figure 2

| Site (Length) | Position | Score | (Gaps) | Occurrence | Exp Value |
|---|---|---|---|---|---|
| Dof2_CS'(6) | 62 | 6 | ( 0) | 1 | 4.75e-01 |
| Dof4_CS(7) | 98 | 6 | ( 0) | 1 | 4.75e-01 |
| Pti4_CS'(6) | 145 | 6 | ( 0) | 1 | 2.75e-01 |
| C1_CS(7) | 302 | 7 | ( 0) | 1 | 4.75e-01 |
| Adh1_US2'(6) | 360 | 6 | ( 0) | 1 | 2.75e-01 |
| Zmhox1a-Sh (1)(11) | 415 | 8 | ( 0) | 1 | 1.06e-02 |
| C1_CS'(7) | 600 | 7 | ( 0) | 1 | 4.75e-01 |

Figure 3

| Factor or Site Name | Loc.(Str.) | Signal Sequence | SITE # |
|---|---|---|---|
| ABRERATCAL | site | 383 (+) MACGYGB | S000507 |
| AGCBOXNPGLB | site | 145 (-) AGCCGCC | S000232 |
| AMMORESVDCRNIA1 | site | 359 (-) GGCCCCGGG | S000376 |
| ANAERO2CONSENSUS | site | 608 (-) AGCAGC | S000478 |
| ARFAT | site | 4 (-) TGTCTC | S000270 |
| ARR1AT | site | 248 (+) NGATT | S000454 |
| ARR1AT | site | 559 (+) NGATT | S000454 |
| ARR1AT | site | 19 (+) NGATT | S000454 |
| ARR1AT | site | 538 (+) NGATT | S000454 |
| ARR1AT | site | 524 (+) NGATT | S000454 |
| ARR1AT | site | 650 (+) NGATT | S000454 |
| ARR1AT | site | 157 (-) NGATT | S000454 |
| ASF1MOTIFCAMV | site | 43 (+) TGACG | S000024 |
| BOXLCOREDCPAL | site | 302 (+) ACCWWCC | S000492 |
| BOXLCOREDCPAL | site | 600 (-) ACCWWCC | S000492 |
| CAATBOX1 | site | 156 (+) CAAT | S000028 |
| CAATBOX1 | site | 12 (-) CAAT | S000028 |
| CAATBOX1 | site | 594 (-) CAAT | S000028 |
| CAATBOX1 | site | 652 (-) CAAT | S000028 |
| CACTFTPPCA1 | site | 39 (+) YACT | S000449 |
| CACTFTPPCA1 | site | 265 (+) YACT | S000449 |
| CACTFTPPCA1 | site | 295 (+) YACT | S000449 |
| CACTFTPPCA1 | site | 31 (-) YACT | S000449 |
| CACTFTPPCA1 | site | 452 (-) YACT | S000449 |
| CAREOSREP1 | site | 107 (+) CAACTC | S000421 |
| CBFHV | site | 180 (+) RYCGAC | S000497 |
| CBFHV | site | 239 (+) RYCGAC | S000497 |
| CBFHV | site | 180 (-) RYCGAC | S000497 |
| CBFHV | site | 239 (-) RYCGAC | S000497 |
| CCAATBOX1 | site | 155 (+) CCAAT | S000030 |
| CELLCYCLESC | site | 78 (+) CACGAAAA | S000031 |
| CGACGOSAMY3 | site | 182 (+) CGACG | S000205 |
| CGACGOSAMY3 | site | 502 (+) CGACG | S000205 |
| CGACGOSAMY3 | site | 214 (-) CGACG | S000205 |
| CGACGOSAMY3 | site | 256 (-) CGACG | S000205 |
| CGACGOSAMY3 | site | 636 (-) CGACG | S000205 |
| CGCGBOXAT | site | 384 (+) VCGCGB | S000501 |
| CGCGBOXAT | site | 389 (+) VCGCGB | S000501 |
| CGCGBOXAT | site | 482 (+) VCGCGB | S000501 |
| CGCGBOXAT | site | 531 (+) VCGCGB | S000501 |
| CGCGBOXAT | site | 391 (+) VCGCGB | S000501 |
| CGCGBOXAT | site | 384 (-) VCGCGB | S000501 |
| CGCGBOXAT | site | 389 (-) VCGCGB | S000501 |
| CGCGBOXAT | site | 482 (-) VCGCGB | S000501 |
| CGCGBOXAT | site | 531 (-) VCGCGB | S000501 |
| CGCGBOXAT | site | 391 (-) VCGCGB | S000501 |
| CPBCSPOR | site | 458 (+) TATTAG | S000491 |
| CRTDREHVCBF2 | site | 180 (+) GTCGAC | S000411 |
| CRTDREHVCBF2 | site | 239 (+) GTCGAC | S000411 |
| CRTDREHVCBF2 | site | 180 (-) GTCGAC | S000411 |
| CRTDREHVCBF2 | site | 239 (-) GTCGAC | S000411 |
| CURECORECR | site | 104 (+) GTAC | S000493 |
| CURECORECR | site | 218 (+) GTAC | S000493 |
| CURECORECR | site | 104 (-) GTAC | S000493 |
| CURECORECR | site | 218 (-) GTAC | S000493 |
| DOFCOREZM | site | 84 (+) AAAG | S000265 |
| DOFCOREZM | site | 99 (+) AAAG | S000265 |
| DOFCOREZM | site | 63 (-) AAAG | S000265 |
| DOFCOREZM | site | 116 (-) AAAG | S000265 |
| DOFCOREZM | site | 166 (-) AAAG | S000265 |
| DPBFCOREDCDC3 | site | 38 (+) ACACNNG | S000292 |
| E2F1OSPCNA | site | 478 (-) GCGGGAAA | S000396 |
| E2FANTRNR | site | 478 (+) TTTCCCGC | S000366 |
| E2FCONSENSUS | site | 12 (+) WTTSSCSS | S000476 |
| E2FCONSENSUS | site | 250 (+) WTTSSCSS | S000476 |
| E2FCONSENSUS | site | 478 (+) WTTSSCSS | S000476 |
| EBOXBNNAPA | site | 39 (+) CANNTG | S000144 |
| EBOXBNNAPA | site | 265 (+) CANNTG | S000144 |
| EBOXBNNAPA | site | 39 (-) CANNTG | S000144 |
| EBOXBNNAPA | site | 265 (-) CANNTG | S000144 |
| EECCRCAH1 | site | 578 (+) GANTTNC | S000494 |
| GATABOX | site | 590 (+) GATA | S000039 |
| GATABOX | site | 135 (-) GATA | S000039 |
| GATABOX | site | 633 (-) GATA | S000039 |
| GCCCORE | site | 145 (-) GCCGCC | S000430 |

Figure 3 Continued

| | | | | | |
|---|---|---|---|---|---|
| GT1CONSENSUS | site | 81 | (+) | GRWAAW | S000198 |
| GT1CONSENSUS | site | 96 | (+) | GRWAAW | S000198 |
| GT1CONSENSUS | site | 190 | (+) | GRWAAW | S000198 |
| GT1CONSENSUS | site | 201 | (+) | GRWAAW | S000198 |
| GT1CONSENSUS | site | 590 | (+) | GRWAAW | S000198 |
| GT1CONSENSUS | site | 476 | (-) | GRWAAW | S000198 |
| GT1CONSENSUS | site | 526 | (-) | GRWAAW | S000198 |
| GT1CONSENSUS | site | 64 | (-) | GRWAAW | S000198 |
| GT1CONSENSUS | site | 477 | (-) | GRWAAW | S000198 |
| GT1GMSCAM4 | site | 81 | (+) | GAAAAA | S000453 |
| GT1GMSCAM4 | site | 96 | (+) | GAAAAA | S000453 |
| GT1GMSCAM4 | site | 190 | (+) | GAAAAA | S000453 |
| GTGANTG10 | site | 523 | (+) | GTGA | S000378 |
| GTGANTG10 | site | 159 | (-) | GTGA | S000378 |
| GTGANTG10 | site | 300 | (-) | GTGA | S000378 |
| HEXAMERATH4 | site | 213 | (+) | CCGTCG | S000146 |
| HEXAMERATH4 | site | 255 | (+) | CCGTCG | S000146 |
| HEXAMERATH4 | site | 182 | (-) | CCGTCG | S000146 |
| IBOXCORE | site | 590 | (+) | GATAA | S000199 |
| INRNTPSADB | site | 22 | (+) | YTCANTYY | S000395 |
| LTRECOREATCOR15 | site | 421 | (+) | CCGAC | S000153 |
| MYBCOREATCYCB1 | site | 546 | (-) | AACGG | S000502 |
| MYBPLANT | site | 301 | (+) | MACCWAMC | S000167 |
| MYBPLANT | site | 600 | (-) | MACCWAMC | S000167 |
| MYBPZM | site | 303 | (+) | CCWACC | S000179 |
| MYBPZM | site | 600 | (-) | CCWACC | S000179 |
| MYBST1 | site | 589 | (+) | GGATA | S000180 |
| MYCCONSENSUSAT | site | 39 | (+) | CANNTG | S000407 |
| MYCCONSENSUSAT | site | 265 | (+) | CANNTG | S000407 |
| MYCCONSENSUSAT | site | 39 | (-) | CANNTG | S000407 |
| MYCCONSENSUSAT | site | 265 | (-) | CANNTG | S000407 |
| NODCON2GM | site | 2 | (-) | CTCTT | S000462 |
| NODCON2GM | site | 554 | (-) | CTCTT | S000462 |
| OSE2ROOTNODULE | site | 2 | (-) | CTCTT | S000468 |
| OSE2ROOTNODULE | site | 554 | (-) | CTCTT | S000468 |
| PALBOXAPC | site | 658 | (+) | CCGTCC | S000137 |
| PALBOXAPC | site | 129 | (-) | CCGTCC | S000137 |
| PALBOXLPC | site | 298 | (+) | YCYYACCWACC | S000138 |
| POLASIG1 | site | 456 | (-) | AATAAA | S000080 |
| POLLEN1LELAT52 | site | 95 | (+) | AGAAA | S000245 |
| POLLEN1LELAT52 | site | 174 | (+) | AGAAA | S000245 |
| POLLEN1LELAT52 | site | 189 | (+) | AGAAA | S000245 |
| POLLEN1LELAT52 | site | 200 | (+) | AGAAA | S000245 |
| PRECONSCRHSP70A | site | 238 | (-) | SCGAYNRNNNNNNNNNNNNNNNHD | S000506 |
| PRECONSCRHSP70A | site | 550 | (-) | SCGAYNRNNNNNNNNNNNNNNNHD | S000506 |
| PYRIMIDINEBOXOSRAMY1A | site | 83 | (-) | CCTTTT | S000259 |
| PYRIMIDINEBOXOSRAMY1A | site | 98 | (-) | CCTTTT | S000259 |
| REALPHALGLHCB21 | site | 602 | (-) | AACCAA | S000362 |
| SEBFCONSSTPR10A | site | 4 | (-) | YTGTCWC | S000391 |
| SEF3MOTIFGM | site | 74 | (+) | AACCCA | S000115 |
| SEF3MOTIFGM | site | 305 | (+) | AACCCA | S000115 |
| SORLIP1AT | site | 291 | (+) | GCCAC | S000482 |
| SORLIP1AT | site | 377 | (+) | GCCAC | S000482 |
| SORLIP2AT | site | 363 | (+) | GGGCC | S000483 |
| SORLIP2AT | site | 357 | (-) | GGGCC | S000483 |
| SREATMSD | site | 589 | (-) | TTATCC | S000470 |
| SURECOREATSULTR11 | site | 4 | (-) | GAGAC | S000499 |
| TRANSINITDICOTS | site | 473 | (-) | AMNAUGGC | S000201 |
| TRANSINITMONOCOTS | site | 473 | (-) | RMNAUGGC | S000202 |
| WBOXATNPR1 | site | 42 | (+) | TTGAC | S000390 |
| WRKY71OS | site | 43 | (+) | TGAC | S000447 |

GENE EXPRESSION CONTROL IN PLANTS

CROSS-REFERENCE TO RELATED APPLICATIONS

This application is a National Stage Application filed under 35 U.S.C. §371 of PCT Application No. PCT/NZ2009/000047, filed on Mar. 30, 2009 and published in English on Oct. 8, 2009 as WO 2009/123479, which claims the benefit of U.S. Provisional Application 61/042,038, filed Apr. 3, 2008, each of which are incorporated by reference in its entirety herein.

TECHNICAL FIELD

The present invention relates to the isolation and use of the polynucleotides for the control of gene expression in plants.

BACKGROUND ART

An important goal for agriculture is to produce plants with agronomically important traits. Recent advances in genetic manipulation provide the tools to transform plants to contain and express foreign genes. This has led to the development of plants capable of expressing pharmaceuticals and other chemicals, plants with increased pest resistance, increased stress tolerance and many other beneficial traits.

It is often desirable to control expression of a polynucleotide of interest, in a particular tissue, at a particular developmental stage, or under particular conditions, in which the polynucleotide is not normally expressed. The polynucleotide of interest may encode a protein or alternatively may be intended to effect silencing of a corresponding target gene.

Plant promoter sequences are useful in genetic manipulation for directing such spatial, temporal and inducible expression of polynucleotides in transgenic plants. To achieve this, a genetic construct is often introduced into a plant cell or plant. Typically such constructs include a plant promoter operably linked to the polynucleotide sequence of interest. Such a promoter need not normally be associated with the gene of interest. Once transformed, the promoter controls expression of the operably linked polynucleotide of interest thus leading to the desired transgene expression and resulting desired phenotypic characteristics in the plant.

Promoters used in genetic manipulation are typically derived from the 5' un-transcribed region of genes and contain regulatory elements that are necessary to control expression of the operably linked polynucleotide. Promoters useful for plant biotechnology can be classified depending on when and where they direct expression. For example promoters may be tissue specific or constitutive (capable of transcribing sequences in multiple tissues). Other classes of promoters include inducible promoters that can be triggered on external stimuli such as environmental, and chemical stimuli.

It would be beneficial to have a variety of promoters available in order to ensure that transgenes are transcribed efficiently in the right tissues, at an appropriate stage of growth or development. Additionally it may be desirable to direct a gene expression in response to certain environmental or chemicals signals.

Perennial ryegrass (*Lolium perenne* L) is the major grass species grown in New Zealand and other temperate climates throughout the world. Valuable traits that may be improved by genetic manipulation of perennial ryegrass include stress tolerance, disease tolerance and nutritional quality. Genetic manipulation of such traits in perennial ryegrass is limited by the availability of promoters capable of appropriately controlling the expression of genes of interest.

It is therefore an object of the present invention to provide a promoter from ryegrass useful for controlling expression of genes in plants or at least to provide a useful choice.

SUMMARY OF THE INVENTION

In one aspect the invention provides an isolated promoter polynucleotide comprising:
  a) the sequence of SEQ ID NO:1;
  b) a variant of the sequence of SEQ ID NO:1;
  c) a fragment of the sequence of SEQ ID NO:1;
  d) a fragment of the sequence of b);
  e) a variant of the sequence of c); or
  f) the complement of any one of a) to e).

In one embodiment the isolated promoter polynucleotide comprises:
  a) the sequence of SEQ ID NO:1;
  b) a sequence with at least 70% identity to the sequence of SEQ ID NO:1;
  c) at least 50 contiguous nucleotides of the sequence of SEQ ID NO:1;
  d) at least 50 contiguous nucleotides of the sequence of b);
  e) a sequence with at least 70% identity to the sequence of c); or
  f) the complement of any one of a) to e).

In a preferred embodiment, the promoter polynucleotide is capable of controlling transcription of an operably linked polynucleotide in a plant.

In one embodiment the promoter polynucleotide is capable of controlling transcription of an operably linked polynucleotide sequence in at least one of leaves, internodes, roots and flowers.

In a further embodiment the promoter polynucleotide is capable of controlling transcription of an operably linked polynucleotide sequence in leaves.

In a further embodiment the promoter polynucleotide is capable of controlling transcription of an operably linked polynucleotide sequence in internodes.

In a further embodiment the promoter polynucleotide is capable of controlling transcription of an operably linked polynucleotide sequence in roots.

In a further embodiment the promoter polynucleotide is capable of controlling transcription of an operably linked polynucleotide sequence in flowers.

Preferably the promoter polynucleotide is capable of driving transcription of an operably linked polynucleotide sequence more prominently in above ground plant parts than in the below ground plant parts.

Preferably the promoter polynucleotide is capable of driving transcription of an operably linked polynucleotide sequence more prominently in leaves and internodes than in roots and flowers.

In a further aspect the invention provides a genetic construct comprising a promoter polynucleotide of the invention.

In one embodiment the promoter polynucleotide is operably linked to a polynucleotide sequence to be expressed.

In a further aspect the invention provides a vector comprising a genetic construct of the invention.

In a further aspect the invention provides a plant cell or plant transformed with the promoter polynucleotide of the invention.

In a further aspect the invention provides a plant cell or plant transformed with a genetic construct of the invention.

In a further aspect the invention provides a method for modifying expression of at least one polynucleotide in a plant cell or plant, the method comprising transformation of the plant cell or plant with a promoter polynucleotide of the invention In a further aspect the invention provides a method for modifying expression of at least one polynucleotide in a plant cell or plant, the method comprising transformation of the plant cell or plant with a genetic construct of the invention.

In a further aspect the invention provides a method for producing a plant cell or plant with modified expression of at least one polynucleotide, the method comprising:
(a) transforming plant cell or plant with a promoter polynucleotide of the invention, and
(b) the cultivating the transgenic plant cell or plant under conditions conducive for the promoter polynucleotide to drive transcription.

In a further aspect the invention provides a method for producing a plant cell or plant with modified expression of at least one polynucleotide, the method comprising:
(a) transforming plant cell or plant with a genetic construct of the invention, and
(b) the cultivating the transgenic plant cell or plant under conditions conducive for the promoter polynucleotide to drive transcription.

In a further aspect the invention provides a method for producing a plant cell or plant with modified expression of at least one gene, the method comprising:
(a) transforming plant cell or plant with a genetic construct of the invention wherein the genetic construct comprises a promoter polynucleotide of the invention operably linked to a polynucleotide sequence to be expressed, and
(b) the cultivating the transgenic plant cell or plant under conditions conducive for the promoter polynucleotide to drive transcription of operably linked sequence.

It will be appreciated by those skilled in the art that, the promoter polynucleotide of the invention may be transformed into the plant to control expression of a polynucleotide operably linked to the promoter prior to transformation. Alternatively the promoter polynucleotide may be transformed into the genome of the plant without an operably linked polynucleotide, but the promoter may control expression of an endogenous polynucleotide, adjacent to the insert site, and typically, to the 3' end of the inserted promoter polynucleotide.

In a further aspect of the invention provides a method for producing a plant cell or plant with a modified phenotype, the method including the stable incorporation into the genome of the plant, a promoter polynucleotide of the invention In a further aspect of the invention provides a method for producing a plant cell or plant with a modified phenotype, the method including the stable incorporation into the genome of the plant, a genetic construct of the invention In a further aspect the invention provides a plant cell or plant produced by a method of the invention.

In a further aspect the invention provides a seed, propagule, progeny or part of a plant, of the invention.

The promoter polynucleotide of the invention may be derived from any species and/or may be produced synthetically or recombinantly.

In one embodiment the promoter polynucleotide, is derived from a plant species.

In a further embodiment the promoter polynucleotide, is derived from a gymnosperm plant species.

In a further embodiment the promoter polynucleotide, is derived from an angiosperm plant species.

In a further embodiment the promoter polynucleotide, is derived from a from dicotyledonuous plant species.

In a further embodiment the promoter polynucleotide, is derived from a monocotyledonous plant species.

The polypeptide encoded by the polynucleotide to be expressed in the construct of the invention, may be derived from any species and/or may be produced synthetically or recombinantly.

In one embodiment the polypeptide is derived from a plant species.

In a further embodiment the polypeptide is derived from a gymnosperm plant species.

In a further embodiment the polypeptide is derived from an angiosperm plant species.

In a further embodiment the polypeptide is derived from a from dicotyledonous plant species.

In a further embodiment the polypeptide is derived from a monocotyledonous plant species.

The plant cells and plants, of the invention may be derived from any species.

In one embodiment the plant cell or plant, is derived from a gymnosperm plant species.

In a further embodiment the plant cell or plant, is derived from an angiosperm plant species.

In a further embodiment the plant cell or plant, is derived from a from dicotyledonous plant species.

In a further embodiment the plant cell or plant, is derived from a monocotyledonous plant species.

Preferred dicotyledonous plant genera include: *Amygdalus, Anacardium, Anemone, Arachis, Beta, Brassica, Cajanus, Cannabis, Carthamus, Carya, Ceiba, Cicer, Claytonia, Coriandrum, Coronilla, Corydalis, Crotalaria, Cyclamen, Dentaria, Dicentra, Dolichos, Eranthis, Glycine, Gossypium, Helianthus, Lathyrus, Lens, Lespedeza, Linum, Lotus, Lupinus, Macadamia, Medicago, Melilotus, Mucuna, Olea, Onobrychis, Ornithopus, Oxalis, Papaver, Phaseolus, Phoenix, Pistacia, Pisum, Prunus, Pueraria, Ribes, Ricinus, Sesamum, Solanum, Thalictrum, Theobroma, Trifolium, Trigonella, Vicia* and *Vigna*.

Preferred dicotyledonous plant species include: *Amygdalus communis, Anacardium occidentale, Anemone americana, Anemone occidentalis, Arachis hypogaea, Arachis hypogea, Beta vulgaris, Brassica napus Rape, Brassica nigra, Brassica campestris, Cajanus cajan, Cajanus indicus, Cannabis sativa, Carthamus tinctorius, Carya illinoinensis, Ceiba pentandra, Cicer arietinum, Claytonia exigua, Claytonia megarhiza, Coriandrum sativum, Coronilla varia, Corydalis flavula, Corydalis sempervirens, Crotalaria juncea, Cyclamen coum, Dentaria laciniata, Dicentra eximia, Dicentra formosa, Dolichos lablab, Eranthis hyemalis, Gossypium arboreum, Gossypium nanking, Gossypium barbadense, Gossypium herbaceum, Gossypium hirsutum, Glycine max, Glycine ussuriensis, Glycine gracilis, Helianthus annus, Lupinus angustifolius, Lupinus luteus, Lupinus mutabilis, Lespedeza sericea, Lespedeza striata, Lotus uliginosus, Lathyrus sativus, Lens culinaris, Lespedeza stipulacea, Linum usitatissimum, Lotus corniculatus, Lupinus albus, Medicago arborea, Medicago falcate, Medicago hispida, Medicago officinalis, Medicago sativa (alfalfa), Medicago tribuloides, Macadamia integrifolia, Medicago arabica, Melilotus albus, Mucuna pruriens, Olea europaea, Onobrychis viciifolia, Ornithopus sativus, Oxalis tuberosa, Phaseolus aureus, Prunus cerasifera, Prunus cerasus, Phaseolus coccineus, Prunus domestica, Phaseolus lunatus, Phaseolus mungo, Phaseolus vulgaris, Papaver somniferum, Phaseolus acutifolius, Phoenix dactylifera, Pistacia vera, Pisum sativum, Prunus amygdalus, Prunus armeniaca, Prunus maheleb, Prunus persica, Prunus pseudocerasus, Pueraria thunbergiana, Ribes nigrum, Ribes rubrum, Ribes grossu-* laria, *Ricinus communis, Sesamum indicum, Solanum lycopersicon, Solanum tuberosum, Thalictrum dioicum, Thalictrum flavum, Thalictrum thalictroides, Theobroma cacao, Trifolium augustifolium, Trifolium diffusum, Trifolium hybridum, Trifolium incarnatum, Trifolium ingrescens, Trifolium pratense, Trifolium repens, Trifolium resupinatum, Trifolium subterraneum, Trifolium alexandrinum, Trigonella foenumgraecum, Vicia angustifolia, Vicia atropurpurea, Vicia calcarata, Vicia dasycarpa, Vicia ervilia, Vaccinium oxycoccos, Vicia pannonica, Vigna sesquipedalis, Vigna sinensis, Vicia villosa, Vicia faba, Vicia sative* and *Vigna angularis.*

Preferred monocotyledonous plant genera include: *Agropyron, Allium, Alopecurus, Andropogon, Arrhenatherum, Asparagus, Avena, Bambusa, Bellavalia, Brimeura, Brodiaea, Bulbocodium, Bothrichloa, Bouteloua, Bromus, Calamovilfa, Camassia, Cenchrus, Chionodoxa, Chloris, Colchicum, Crocus, Cymbopogon, Cynodon, Cypripedium, Dactylis, Dichanthium, Digitaria, Elaeis, Eleusine, Eragrostis, Eremurus, Erythronium, Fagopyrum, Festuca, Fritillaria, Galanthus, Helianthus, Hordeum, Hyacinthus, Hyacinthoides, Ipheion, Iris, Leucojum, Liatris, Lolium, Lycoris, Miscanthis, Miscanthus x giganteus, Muscari, Ornithogalum, Oryza, Panicum, Paspalum, Pennisetum, Phalaris, Phlem, Poa, Puschkinia, Saccharum, Secale, Setaria, Sorghastrum, Sorghum, Triticum, Vanilla, X Triticosecale, Triticale* and *Zea.*

Preferred monocotyledonous plant species include: *Agropyron cristatum, Agropyron desertorum, Agropyron elongatum, Agropyron intermedium, Agropyron smithii, Agropyron spicatum, Agropyron trachycaulum, Agropyron trichophorum, Allium ascalonicum, Allium cepa, Allium chinense, Allium porrum, Allium schoenoprasum, Allium fistulosum, Allium sativum, Alopecurus pratensis, Andropogon gerardi, Andropogon gerardii, Andropogon scoparious, Arrhenatherum elatius, Asparagus officinalis, Avena nuda, Avena sativa, Bambusa vulgaris, Bellevalia trifoliate, Brimeura amethystina, Brodiaea californica, Brodiaea coronaria, Brodiaea elegans, Bulbocodium versicolor, Bothrichloa barbinodis, Bothrichloa ischaemum, Bothrichloa saccharoides, Bouteloua curipendula, Bouteloua eriopoda, Bouteloua gracilis, Bromus erectus, Bromus inermis, Bromus riparius, Calamovilfa longifilia, Camassia scilloides, Cenchrus ciliaris, Chionodoxa forbesii, Chloris gayana, Colchicum autumnale, Crocus sativus, Cymbopogon nardus, Cynodon dactylon, Cypripedium acaule, Dactylis glomerata, Dichanthium annulatum, Dichanthium aristatum, Dichanthium sericeum, Digitaria decumbens, Digitaria smutsii, Elaeis guineensis, Elaeis oleifera, Eleusine coracan, Elymus angustus, Elymus junceus, Eragrostis curvula, Eragrostis tef Eremurus robustus, Erythronium elegans, Erythronium helenae, Fagopyrum esculentum, Fagopyrum tataricum, Festuca arundinacea, Festuca ovina, Festuca pratensis, Festuca rubra, Festu-lolium, Fritillaria cirrhosa, Galanthus nivalis, Helianthus annuus sunflower, Hordeum distichum, Hordeum vulgare, Hyacinthus orientalis, Hyacinthoides hispanica, Hyacinthoides non-scripta, Ipheion sessile, Iris collettii, Iris danfordiae, Iris reticulate, Leucojum aestivum, Liatris cylindracea, Liatris elegans, Lilium longiflorum, Lolium multiflorum, Lolium perenne, Lycoris radiata, Miscanthis sinensis, Miscanthus x giganteus, Muscari armeniacum, Muscari macrocarpum, Narcissus pseudonarcissus, Ornithogalum montanum, Oryza glaberrima, Oryza longistaminata, Oryza ruflpogon, Oryza sativa, Panicum italicium, Panicum maximum, Panicum miliaceum, Panicum purpurascens, Panicum virgatum, Panicum virgatum, Paspalum dilatatum, Paspalum notatum, Pennisetum clandestinum, Pennisetum glaucum, Pennisetum purpureum, Pennisetum spicatum, Phalaris arundinacea, Phleum bertolinii, Phleum pratense, Poa fendleriana, Poa pratensis, Poa nemoralis, Puschkinia scilloides, Saccharum officinarum, Saccharum robustum, Saccharum sinense, Saccharum spontaneum, Scilla autumnalis, Scilla peruviana, Secale cereale, Setaria italica, Setaria sphacelata, Sorghastrum nutans, Sorghum bicolor, Sorghum dochna, Sorghum halepense, Sorghum sudanense, Trillium grandiflorum, Triticum aestivum, Triticum dicoccum, Triticum durum, Triticum monococcum, Tulipa batalinii, Tulipa clusiana, Tulipa dasystemon, Tulipa gesneriana, Tulipa greigii, Tulipa kaufinanniana, Tulipa sylvestris, Tulipa turkestanica, Vanilla fragrans, X Triticosecale* and *Zea mays.*

Other preferred plants are forage plants from a group comprising but not limited to the following genera: *Lolium, Festuca, Dactylis, Bromus, Trifolium, Medicago, Phleum, Phalaris, Holcus, Lotus, Plantago* and *Cichorium.*

Particularly preferred forage plants are from the genera *Lolium* and *Trifolium.* Particularly preferred species are *Lolium perenne* and *Trifolium repens.*

Particularly preferred monocotyledonous plant species are: *Lolium perenne, Oryza sativa* and *Zea mays.*

A preferred monocotyledonous plant species is *Zea mays.*

Another preferred monocotyledonous plant species is *Oryza sativa.*

A particularly preferred plant species is *Lolium perenne.*

DETAILED DESCRIPTION

The applicants have identified a promoter polynucleotide sequence from perennial ryegrass (*Lolium perenne*) and demonstrated that the promoter regulates transcription of an operably linked polynucleotide in at least one of leaves, internodes, roots and flowers. The invention also provides variants and fragments of the promoter polynucleotide. The invention provides genetic constructs and vectors comprising the promoter polynucleotide sequences, and transgenic plant cells and transgenic plants comprising the promoter polynucleotide sequence, genetic constructs, or vectors of the invention.

The invention also provides methods for modifying expression of genes in plants and modifying phenotype in plants, and methods for producing plants with modified gene expression and modified phenotype. The invention further provides plants produced by the methods of the invention.

The term "comprising" as used in this specification and claims means "consisting at least in part of"; that is to say when interpreting statements in this specification and claims which include "comprising", the features prefaced by this term in each statement all need to be present but other features can also be present. Related terms such as "comprise" and "comprised" are to be interpreted in similar manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

A "fragment" of a polynucleotide sequence provided herein is a subsequence of contiguous nucleotides that is preferably at least 15 nucleotides in length. The fragments of the invention preferably comprises at least 20 nucleotides, more preferably at least 30 nucleotides, more preferably at least 40 nucleotides, more preferably at least 50 nucleotides and most preferably at least 60 contiguous nucleotides of a polynucleotide of the invention. A fragment of a polynucleotide sequence can be used in antisense, gene silencing, triple helix or ribozyme technology, or as a primer, a probe, included in a microarray, or used in polynucleotide-based selection methods.

The term "fragment" in relation to promoter polynucleotide sequences is intended to include sequences comprising cis-elements and regions of the promoter polynucleotide sequence capable of regulating expression of a polynucleotide sequence to which the fragment is operably linked.

Preferably fragments of promoter polynucleotide sequences of the invention comprise at least 20, more preferably at least 30, more preferably at least 40, more preferably at least 50, more preferably at least 100, more preferably at least 200, more preferably at least 300, more preferably at least 400, more preferably at least 500, most preferably at least 600 contiguous nucleotides of a promoter polynucleotide of the invention.

Preferably fragments of promoter polynucleotide sequences of the invention comprise at least one copy of one and most preferably at least one copy of two of the two light-inducible promoter motifs: AGCCAC (SORLIP1) and GGGCC (SORLIP2); in addition to at least one copy of one or more preferably at least one copy of two CCGTCG (Hexamer promoter motif); in addition to at least one copy of one or more preferably at least one copy of two GTAC (CuRE—copper response element); in addition to at least one copy of one or more preferably at least one copy of two or more preferably at least one copy of three or most preferably at least one copy of four of AGAANNTTnn (HSEs-like binding site motif); in addition to at least one copy of one ACACTTG (DPBF1&2 binding site motif) and/or TCCCGACCA (DRE-like promoter motif) and/or TTTCCCGC (E2F binding site motif) and/or CACCAACC (MYB binding site promoter) motifs.

The term "primer" refers to a short polynucleotide, usually having a free 3'OH group, that is hybridized to a template and used for priming polymerization of a polynucleotide complementary to the template. Such a primer is preferably at least 5, more preferably at least 6, more preferably at least 7, more preferably at least 9, more preferably at least 10, more preferably at least 11, more preferably at least 12, more preferably at least 13, more preferably at least 14, more preferably at least 15, more preferably at least 16, more preferably at least 17, more preferably at least 18, more preferably at least 19, more preferably at least 20 nucleotides in length.

The term "probe" refers to a short polynucleotide that is used to detect a polynucleotide sequence, that is complementary to the probe, in a hybridization-based assay. The probe may consist of a "fragment" of a polynucleotide as defined herein. Preferably such a probe is at least 5, more preferably at least 10, more preferably at least 20, more preferably at least 30, more preferably at least 40, more preferably at least 50, more preferably at least 100, more preferably at least 200, more preferably at least 300, more preferably at least 400 and most preferably at least 500 nucleotides in length.

The term "derived from" with respect to polynucleotides of the invention being "derived from" a particular genera or species, means that the polynucleotide has the same sequence as a polynucleotide found naturally in that genera or species. The polynucleotide which is derived from a genera or species may therefore be produced synthetically or recombinantly.

Polypeptides and Fragments

The term "polypeptide", as used herein, encompasses amino acid chains of any length but preferably at least 5 amino acids, including full-length proteins, in which amino acid residues are linked by covalent peptide bonds. The polypeptides may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "fragment" of a polypeptide is a subsequence of the polypeptide that performs a function that is required for the biological activity and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing the above enzymatic activity.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

The term "derived from" with respect to polypeptides disclosed being derived from a particular genera or species, means that the polypeptide has the same sequence as a polypeptide found naturally in that genera or species. The polypeptide, derived from a particular genera or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polynucleotides and polypeptides possess biological activities that are the same or similar to those of the inventive polynucleotides or polypeptides. The term "variant" with reference to polynucleotides and polypeptides encompasses all forms of polynucleotides and polypeptides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a specified polynucleotide sequence. Identity is found over a comparison window of at least 20 nucleotide positions, more preferably at least 50 nucleotide positions, more preferably at least 100 nucleotide positions, more preferably at least 200 nucleotide positions, more preferably at least 300 nucleotide positions, more preferably at least 400 nucleotide positions, more preferably at least 500 nucleotide positions, more preferably at least 600 nucleotide positions, and most preferably over the entire length of the specified polynucleotide sequence.

Variant promoter polynucleotides of the invention preferably comprise at least one copy of one and most preferably at least one copy of two of the two light-inducible promoter motifs: AGCCAC (SORLIP1) and GGGCC (SORLIP2); in addition to at least one copy of one or more preferably at least one copy of two CCGTCG (Hexamer promoter motif); in addition to at least one copy of one or more preferably at least one copy of two GTAC (CuRE—copper response element); in addition to at least one copy of one or more preferably at least one copy of two or more preferably at least one copy of three or most preferably at least one copy of four of AGAANNTTnn (HSEs-like binding site motif); in addition to at least one copy of one ACACTTG (DPBF1&2 binding site motif) and/or TCCCGACCA (DRE-like promoter motif) and/or TTTCCCGC (E2F binding site motif) and/or CAC-CAACC (MYB binding site promoter) motifs.

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from NCBI (ftp://ftp.ncbi.nih.gov/blast/). The default parameters of bl2seq are utilized except that filtering of low complexity parts should be turned off.

The identity of polynucleotide sequences may be examined using the following unix command line parameters:
bl2seq–nucleotideseq1–j nucleotideseq2–F F–p blastn The parameter –F F turns off filtering of low complexity sections. The parameter –p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from http: www<dot>hgmp<dot>mrc<dot>ac<dot>uk/Software/EMBOSSI. The European Bioinformatics Institute server also provides the facility to perform EMBOSS-needle global alignments between two sequences on line at http: www<dot>ebi<dot>ac<dot>uk/emboss/align/.

Alternatively the GAP program, which computes an optimal global alignment of two sequences without penalizing terminal gaps, may be used to calculate sequence identity. GAP is described in the following paper: Huang, X. (1994) On Global Sequence Alignment. Computer Applications in the Biosciences 10, 227-235.

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polynucleotides may be determined using the publicly available bl2seq program from the BLAST suite of programs (version 2.2.5 [November 2002]) from NCBI (ftp://ftp.ncbi.nih.gov/blast/).

The similarity of polynucleotide sequences may be examined using the following unix command line parameters:
bl2seq–i nucleotideseq1–j nucleotideseq2–F F–p tblastx The parameter –F F turns off filtering of low complexity sections. The parameter –p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1\times10^{-10}$ more preferably less than $1\times10^{-20}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$ and most preferably less than $1\times10^{-100}$ when compared with any one of the specifically identified sequences.

Alternatively, variant polynucleotides of the present invention hybridize to a specified polynucleotide sequence, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing,). Tm for polynucleotide molecules greater than about 100 bases can be calculated by the formula Tm=81.5+0.41% (G+C−log (Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6× SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides such as those in constructs of the invention encoding stress-protective protein, also encompasses polynucleotides that differ from the specified sequences but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also contemplated. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [November 2002]) from NCBI (ftp://ftp.ncbi.nih.gov/blast/) via the tblastx algorithm as previously described.

Constructs, Vectors and Components Thereof

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain a promoter polynucleotide such as a promoter polynucleotide of the invention including the necessary elements that permit transcribing the insert polynucleotide molecule, and, optionally, translating the transcript into a polypeptide. The insert polynucleotide molecule may be derived from the host cell, or may be derived from a different cell or organism and/or may be a synthetic or recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as E. coli.

The term "expression construct" refers to a genetic construct that includes the necessary elements that permit transcribing the insert polynucleotide molecule, and, optionally, translating the transcript into a polypeptide. An expression construct typically comprises in a 5' to 3' direction:
 a) a promoter, such as a promoter polynucleotide sequence of the invention, functional in the host cell into which the construct will be transformed,
 b) the polynucleotide to be expressed, and
 c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

The term "noncoding region" includes to untranslated sequences that are upstream of the translational start site and downstream of the translational stop site. These sequences are also referred to respectively as the 5' UTR and the 3' UTR. These sequences may include elements required for transcription initiation and termination and for regulation of translation efficiency. The term "noncoding" also includes intronic sequences within genomic clones.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to a polynucleotide sequence capable of regulating the expression of a polynucleotide sequence to which the promoter is operably linked. Promoters may comprise cis-initiator elements which specify the transcription initiation site and conserved boxes such as the TATA box, and motifs that are bound by transcription factors.

Methods for Isolating or Producing Polynucleotides

The polynucleotide molecules of the invention can be isolated by using a variety of techniques known to those of ordinary skill in the art. By way of example, such polynucleotides can be isolated through use of the polymerase chain reaction (PCR) described in Mullis et al., Eds. 1994 The Polymerase Chain Reaction, Birkhauser, incorporated herein by reference. The polynucleotides of the invention can be amplified using primers, as defined herein, derived from the polynucleotide sequences of the invention.

Further methods for isolating polynucleotides of the invention, or useful in the methods of the invention, include use of all or portions, of the polynucleotides set forth herein as hybridization probes. The technique of hybridizing labeled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5.0×SSC, 0.5% sodium dodecyl sulfate, 1×Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1×SSC, 1% (w/v) sodium dodecyl sulfate, at 60° C.

The polynucleotide fragments of the invention may be produced by techniques well-known in the art such as restriction endonuclease digestion, oligonucleotide synthesis and PCR amplification.

A partial polynucleotide sequence may be used, in methods well-known in the art to identify the corresponding full length polynucleotide sequence. Such methods include PCR-based methods, 5'RACE (Frohman M A, 1993, Methods Enzymol. 218: 340-56) and hybridization-based method, computer/database—based methods. Further, by way of example, inverse PCR permits acquisition of unknown sequences, flanking the polynucleotide sequences disclosed herein, starting with primers based on a known region (Triglia et al., 1998, *Nucleic Acids Res* 16, 8186, incorporated herein by reference). The method uses several restriction enzymes to generate a suitable fragment in the known region of a polynucleotide. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilise a sequence identical (or at least highly similar) to that in the plant, for which reduced expression is desired. For these reasons among others, it is desirable to be able to identify and isolate orthologues of a particular gene in several different plant species. Variants (including orthologues) may be identified by the methods described.

The promoter sequences disclosed may be characterized to identify fragments, such as cis-elements and regions, capable of regulating to expression of operably linked sequences, using techniques well-known to those skilled in the art. Such techniques include 5' and/or 3' deletion analysis, linker scanning analysis and various DNA footprinting techniques (Degenhardt et al., 1994 Plant Cell: 6(8) 1123-34; *Directed Mutagenesis: A Practical Approach IRL Press* (1991)). Fragments include truncated versions of longer promoter sequences which may terminate (at the 3' end) at or close to the transcriptional start site. Methods for identifying the transcription start site of a promoter are well-known to those skilled in the art (discussed in Hashimoto et al., 2004, Nature Biotechnology 22, 1146-1149).

The techniques described above may be used to identify a fragment that defines essential region of the promoter that is able to confer the desired expression profile. The essential region may function by itself or may be fused to a core promoter to drive expression of an operably linked polynucleotide.

The core promoter can be any one of known core promoters such as the Cauliflower Mosaic Virus 35S or 19S promoter (U.S. Pat. No. 5,352,605), ubiquitin promoter (U.S. Pat. No. 5,510,474) the 1N2 core promoter (U.S. Pat. No. 5,364,780) or a Figwort Mosaic Virus promoter (Gruber, et al. "Vectors for Plant Transformation" *Methods in Plant Molecular Biology and Biotechnology*) et al. eds, CRC Press pp. 89-119 (1993)).

Promoter fragments can be tested for their utility in driving expression in any particular cell or tissue type, or at any particular developmental stage, or in response to any particular stimulus by techniques well-known to those skilled in the art. Techniques include operably-linking the promoter fragment to a reporter or other polynucleotide and measuring report activity or polynucleotide expressions in plants in response to stress. Such techniques are described in the Examples section of this specification.

Methods for Identifying Variants

Physical Methods

Variant polynucleotides may be identified using PCR-based methods (Mullis et al., Eds. 1994 The Polymerase Chain Reaction, Birkhauser).

Alternatively library screening methods, well known to those skilled in the art, may be employed (Sambrook et al., Molecular Cloning: A Laboratory Manual, 2nd Ed. Cold Spring Harbor Press, 1987). When identifying variants of the probe sequence, hybridization and/or wash stringency will typically be reduced relatively to when exact sequence matches are sought.

Computer-Based Methods

Polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from (ftp://ftp.ncbi.nih.gov/blast/) or from the National Center for Biotechnology Information (NCBI), National Library of Medicine, Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680, http www-igbmc<dot>u-strasbg<dot>fr/BioInfolClustalW/Top<dot>html) or T-COF-FEE (Cedric Notredame, Desmond G. Higgins, Jaap Hering a, T-Coffee: A novel method for fast and accurate multiple sequence alignment, J. Mol. Biol. (2000) 302: 205-217)) or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (www<dot>expasy<dot>org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Methods for Producing Constructs and Vectors

The genetic constructs of the present invention comprise one or more polynucleotide sequences of the invention and/or polynucleotides encoding polypeptides disclosed, and may be useful for transforming, for example, bacterial, fungal, insect, mammalian or particularly plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising constructs and Vectors

The invention provides a host cell which comprises a genetic construct or vector of the invention. Host cells may be derived from, for example, bacterial, fungal, insect, mammalian or plant organisms.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Methods for Producing Plant Cells and Plants Comprising Constructs and Vectors

The invention further provides plant cells which comprise a genetic construct of the invention, and plant cells modified to alter expression of a polynucleotide or polypeptide. Plants comprising such cells also form an aspect of the invention.

Methods for transforming plant cells, plants and portions thereof with polynucleotides are described in Draper et al., 1988, Plant Genetic Transformation and Gene Expression. A Laboratory Manual, Blackwell Sci. Pub. Oxford, p. 365; Potrykus and Spangenburg, 1995, Gene Transfer to Plants. Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

The following are representative publications disclosing genetic transformation protocols that can be used to genetically transform the following plant species: Rice (Alam et al., 1999, Plant Cell Rep. 18, 572); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9:821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); perennial ryegrass (Bajaj et al., 2006, Plant Cell Rep. 25, 651); grasses (U.S. Pat. Nos. 5,187,073, 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792,935); soybean (U.S. Pat. Nos. 5,416,011; 5,569,834; 5,824,877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); brassica (U.S. Pat. Nos. 5,188,958; 5,463,174 and 5,750,871); and cereals (U.S. Pat. No. 6,074,877). Other species are contemplated and suitable methods and protocols are available in the scientific literature for use by those skilled in the art.

Methods for Genetic Manipulation of Plants

A number of strategies for genetically manipulating plants are available (e.g. Birch, 1997, Ann Rev Plant Phys Plant Mol Biol, 48, 297). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. Strategies may also be designed to increase expression of a polynucleotide/polypeptide in response to external stimuli, such as environmental stimuli. Environmental stimuli may include environmental stresses such as mechanical (such as herbivore activity), dehydration, salinity and temperature stresses. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed or to reduce expression of a polynucleotide/polypeptide in response to an external stimuli. Such strategies are known as gene silencing strategies.

Genetic constructs for expression of genes in transgenic plants typically include promoters, such as promoter polynucleotides of the invention, for driving the expression of one or more cloned polynucleotide, terminators and selectable marker sequences to detect presence of the genetic construct in the transformed plant.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zin gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenbert. Eds) Springer Verlag. Berline, pp. 325-336.

Gene silencing strategies may be focused on the gene itself or regulatory elements which effect expression of the encoded polypeptide. "Regulatory elements" is used here in the widest possible sense and includes other genes which interact with the gene of interest.

Genetic constructs designed to decrease or silence the expression of a polynucleotide/polypeptide may include an antisense copy of a polynucleotide. In such constructs the polynucleotide is placed in an antisense orientation with respect to the promoter and terminator.

An "antisense" polynucleotide is obtained by inverting a polynucleotide or a segment of the polynucleotide so that the transcript produced will be complementary to the mRNA transcript of the gene, e.g.,

```
5'GATCTA 3'            3'CTAGAT 5'
(coding strand)        (antisense strand)

3'CUAGAU 5' mRNA       5'GAUCUCG 3' antisense RNA
```

Genetic constructs designed for gene silencing may also include an inverted repeat. An 'inverted repeat' is a sequence that is repeated where the second half of the repeat is in the complementary strand, e.g.,

```
5'-GATCTA.........TAGATC-3'
3'-CTAGAT.........ATCTAG-5'
```

The transcript formed may undergo complementary base pairing to form a hairpin structure. Usually a spacer of at least 3-5 bp between the repeated region is required to allow hairpin formation.

Another silencing approach involves the use of a small antisense RNA targeted to the transcript equivalent to an miRNA (Llave et al., 2002, Science 297, 2053). Use of such small antisense RNA corresponding to polynucleotide of the invention is expressly contemplated.

The term genetic construct as used herein also includes small antisense RNAs and other such polypeptides effecting gene silencing.

Transformation with an expression construct, as herein defined, may also result in gene silencing through a process known as sense suppression (e.g. Napoli et al., 1990, Plant Cell 2, 279; de Carvalho Niebel et al., 1995, Plant Cell, 7, 347). In some cases sense suppression may involve overexpression of the whole or a partial coding sequence but may also involve expression of non-coding region of the gene, such as an intron or a 5' or 3' untranslated region (UTR). Chimeric partial sense constructs can be used to coordinately silence multiple genes (Abbott et al., 2002, Plant Physiol. 128(3): 844-53; Jones et al., 1998, Planta 204: 499-505). The use of such sense suppression strategies to silence the expression of a sequence operably-linked to promoter of the invention is also contemplated.

The polynucleotide inserts in genetic constructs designed for gene silencing may correspond to coding sequence and/or non-coding sequence, such as promoter and/or intron and/or 5' or 3' UTR sequence, or the corresponding gene.

Other gene silencing strategies include dominant negative approaches and the use of ribozyme constructs (McIntyre, 1996, Transgenic Res, 5, 257)

Pre-transcriptional silencing may be brought about through mutation of the gene itself or its regulatory elements. Such mutations may include point mutations, frameshifts, insertions, deletions and substitutions.

Plants

The term "plant" is intended to include a whole plant or any part of a plant, propagules and progeny of a plant.

The term 'propagule' means any part of a plant that may be used in reproduction or propagation, either sexual or asexual, including seeds and cuttings.

A "transgenic" or transformed" plant refers to a plant which contains new genetic material as a result of genetic manipulation or transformation. The new genetic material may be derived from a plant of the same species as the resulting transgenic or transformed plant or from a different species. A transformed plant includes a plant which is either stably or transiently transformed with new genetic material.

The plants of the invention may be grown and either self-ed or crossed with a different plant strain and the resulting hybrids, with the desired phenotypic characteristics, may be identified. Two or more generations may be grown. Plants resulting from such standard breeding approaches also form an aspect of the present invention.

BRIEF DESCRIPTION OF THE DRAWINGS

FIG. 1 shows the promoter polynucleotide sequence of SEQ ID NO:1, showing the predicted transcription start site (underlined uppercase C).

FIG. 2 shows results of a Tf sitescan/dynamicPlus (available from the world wide web at http:www<dot>iffi<dot>org) (Ghosh D. 2000, Nucleic Acids Research 28:308-10) analysis of the promoter of SEQ ID NO:1.

FIG. 3 shows the results of Signal Scan (available from the world wide web at http:www<dot>dna<dot>affrc<dot>go<dot>jp/PLACE/signalscan<dot>html) analysis of the promoter of SEQ ID NO:1.

EXAMPLES

The invention will now be illustrated with reference to the following non-limiting examples.

Example 1

Identification and Characterisation of the Ryegrass Promoter Sequence of the Invention Hypomethylated genomic DNA from *Lolium perenne* cv. Bronsyn was isolated and sequenced (Orion Genomics, St Louis). A hypomethylated genomic DNA sequence of 664 bp (SEQ ID NO:1) was identified as containing a 5' transcriptional regulatory region based on the sequence homology to a 5' CDS. A set of 4 nested primers were designed (Flanking forward primer SEQ ID NO:3 GCACTACATCCGTTAT-GAAG; Flanking reverse primer SEQ ID NO:4 CGAACGTCTTGGTCAGGAAC; Nested forward primer SEQ ID NO:5 CAAGAGACAAAATTGCCGGG; and Nested reverse primer SEQ ID NO: 6 TGGACGGATCAAT-CAAACCG) to enable us to clone the promoter from the targeted *Lolium perenne* genomic DNA.

The applicants predicted the transcription start site using tools available at http: www<dot>fruitfly<dot>org/seq_tools/promoter<dot>html, the result is shown in FIG. 1.

The applicants used both Tf site scan/dynamicPlus (http:www<dot>ifti<dot>org) (Ghosh D. 2000, NAR, 28:308-10) and Signal Scan (http:www<dot>dna<dot>affrc<dot>go<dot>jp/PLACE/signalscan<dot>html) to identify transcription factor binding sites and cis-acting elements in the sequence of SEQ ID NO:1 The results are shown in FIGS. 2 and 3 respectively.

Of the motifs identified, the following motifs are very likely to have an impact as to the manner in which the promoter functions:

SORLIP1 (AGCCAC)—light activated
SORLIP2 (GGGCC)—light activated
Hexamer promoter motif (CCGTCG)
CuRE—copper response element (GTAC)
HSEs-like binding site motif (AGAANNTTnn)
DPBF1&2 binding site motif (ACACTTG)
DRE-like promoter motif (TCCCGACCA)
E2F binding site motif (TTTCCCGC)
MYB binding site promoter (CACCAACC)

Example 2

Demonstration of Control of Gene Expression By the Ryegrass Promoter of the Invention.

Preparation of a Promoter Reporter Construct

Figure 5:
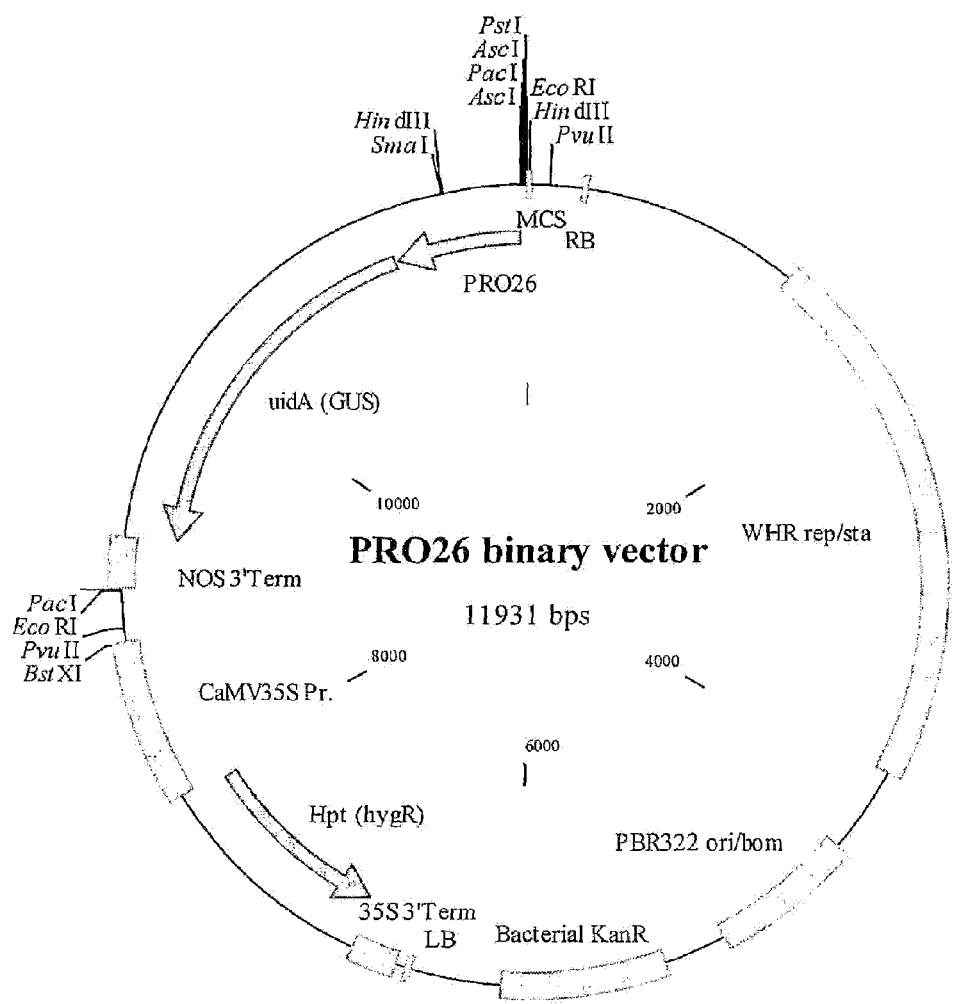
FIG. 5 shows the map of a binary vector including PRO26 operably linked to the bacterial uidA gene.

A 664 bp DNA sequence fragment was amplified by PCR from the sequence of SEQ ID NO:1 using two pairs of oligonucleotide sequences (SEQ ID NO: 1 to 6) and inserted into a T-tailed cloning entry vector that enables a transcriptional fusion between the ryegrass promoter and the GUS reporter gene (Jefferson R. A., et al., 1987. EMBO 6:3901-3907). Clones were sequenced and a positive clone was selected based on sequence analysis indicating that the promoter is in the correct orientation to drive the reporter gene. The promoter-reporter and terminator cassette was excised by digesting with the restriction enzyme PacI. The PacI fragment was ligated in the binary vector at the PacI site to result in the PRO26 binary construct. A map of the PRO26 binary construct is shown in FIG. 5. The sequence of the binary construct is shown in SE ID NO:2.

Table 1 below shows features of the PRO26 construct.

TABLE 1

Molecule: PRO26, 11931 bps DNA Circular

| Type | Start | End | C* | Name | Description |
|---|---|---|---|---|---|
| REGION | 261 | 286 | | RB | |
| REGION | 6520 | 6545 | | LB | |
| REGION | 6810 | 6595 | C | 35S 3'Term | |
| GENE | 7861 | 6839 | C | Hpt | |
| Promoter | 8678 | 7897 | C | DCaMV35S Pr. | |
| REGION | 9179 | 8937 | C | NOS 3'Term | |
| GENE | 11214 | 9190 | C | uidA | GUS encoding gene with intron |
| Promoter | 11895 | 11230 | C | PRO26 | |

Note:
C* = Complimentary sequence

Control Construct

Figure 7:
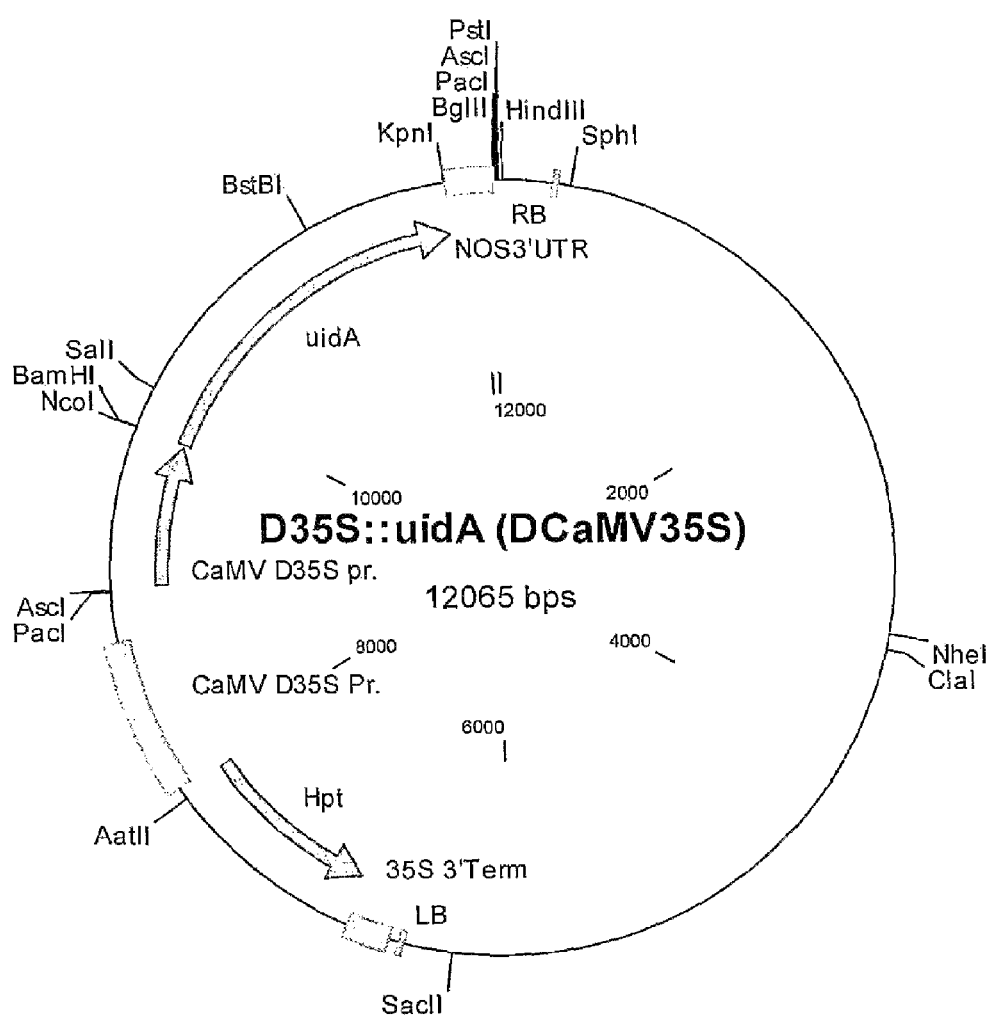
FIG. 7 shows a map of the binary vector D35S::uidA (DCaMV35S) including CaMV D35S promoter operably linked to the bacterial uidA gene.

A control construct with a double CaMV35 promoter driving expression of the GUS reporter gene was also prepared by standard techniques. The sequence of the double CaMV35S promoter used is shown in SEQ ID NO: 7. The sequence of the whole construct is shown in SEQ ID NO: 8. A map of the control construct is shown in FIG. 7.

Table 2 below shows features of the binary construct (D35S::uidA [DCAMV35S]).

TABLE 2

Molecule: D35S::uidA (DCaMV35S),
12065 bps DNA Circular

| Start | End | | Name |
|---|---|---|---|
| 261 | 286 | | RB |
| 6520 | 6545 | | LB |
| 6810 | 6595 | C* | 35S 3'Term |
| 7861 | 6839 | C* | Hpt |
| 8678 | 7894 | C* | CaMV D35S Pr. |
| 8953 | 9749 | | CaMV D35S pr. |
| 9767 | 11792 | | uidA |
| 11802 | 12038 | | NOS3'UTR |

Note:
C* = Complimentary sequence

Plant Transformation

Figure 6:
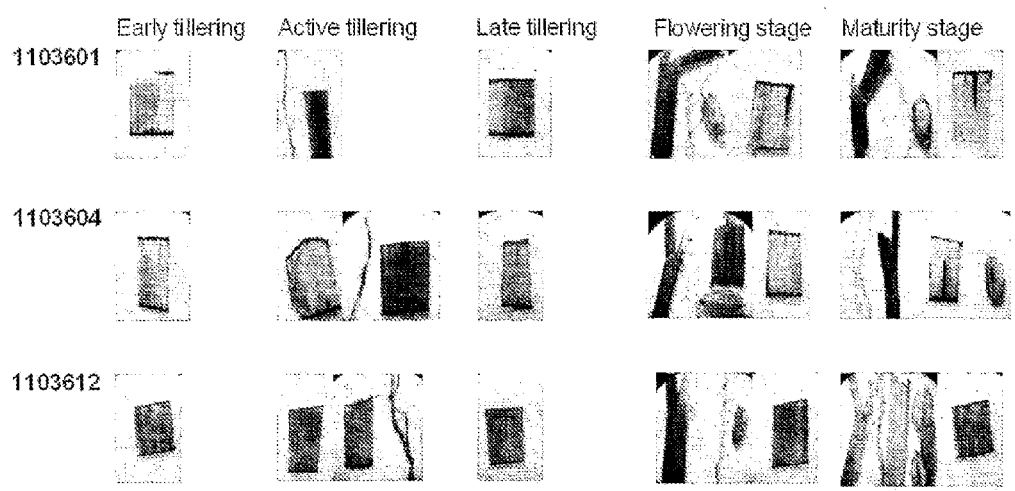
FIG. 6 shows the results from histochemical examination for bacterial uidA expression by GUS activity analysis in two independent transgenic lines of rice.

Rice (*Oryza sativa* spp *japonica* cv. Niponbarre) was transformed using an immature embryo based system (Metahelix Life Sciences, India). Immature panicles, post-milky stage were used to source embryos. Freshly isolated immature embryos were co-cultivated with *Agrobacterium tumefaciens* (*A. tumefaciens*) harboring the promoter/GUS binary construct (PRO26) and control construct described above for 48-64 h. *A. tumefaciens* were eliminated by antibiotic treatment and the explants were transferred to selection medium where the transformed plant cells proliferate to give rise to uniformly transformed calli. The selection medium had a combination of 2,4-D and benzylaminopurine. After 3-4 weeks of selection, the calli were transferred to a regeneration medium containing increased cytokinin and decreased auxin concentration relative to the selection medium. Shoot and root were initiated in this medium. Plantlets were transferred to a glasshouse for hardening. Seven (T$_0$) plants from six independent transformation events were established in the glasshouse. Twenty seeds each from three of the six T$_0$ events were grown to produce T$_1$ plants, which were pheotyped for GUS expression and activity (Tables 2 and 3; FIG. 6).

Figure 4:
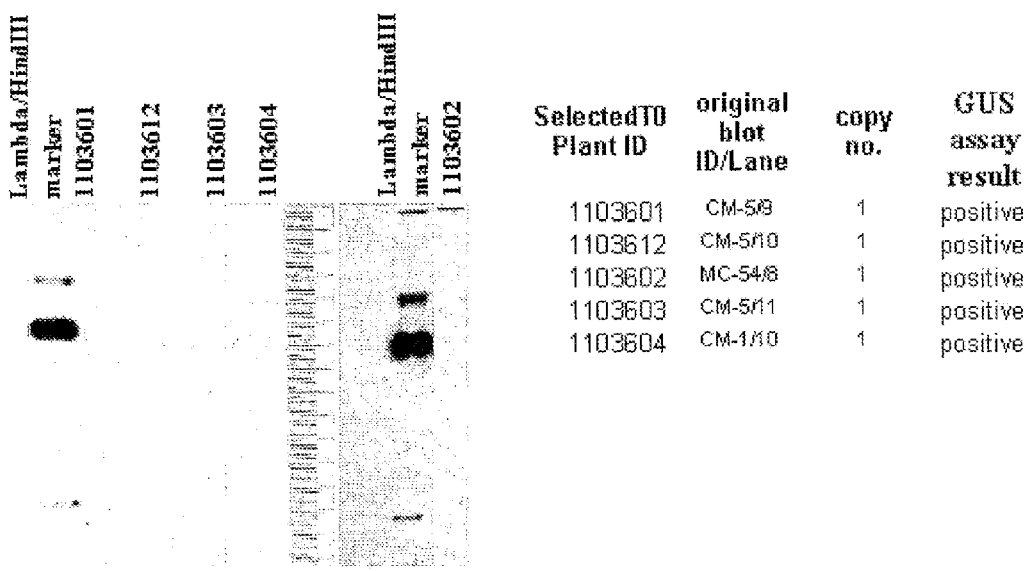
FIG. 4 shows a DNA gel-blot analysis of transgenic (T0) rice lines (1103601, 1103602, 1103603, 1103604, 1103612) transformed with the bacterial uidA gene driven by PRO26.

Perennial ryegrass (*Lolium perenne* L. cv. Tolosa) was transformed essentially as described in Bajaj et. al. (Plant Cell Reports 2006 25: 651-659). Embryogenic callus derived from mersitematic regions of the tillers of selected ryegrass lines and *Agrobacterium tumefaciens* strain EHA101 carrying a modified binary vector (FIG. 4) were used for transformation experiments. Embryogenic calli were immersed with overnight-grown *Agrobacterium* cultures for 30 minutes with continuous shaking. Galli resistant to hygromycin were selected after subculturing them on co-cultivation medium for 4 weeks. After selection, the resistant calli were subcultured on regeneration medium every 2 weeks until the plants regenerated. The regenerants that continued to grow after two or three rounds of selection proved to be stable transformants. Each regenerated plant was then multiplied on maintenance medium to produce clonal plantlets and subsequently rooted on MS medium without hormones. A rooted plant from each clone was transferred into contained glasshouse conditions while retaining a clonal counterpart in tissue culture as backup.

Tissue Specificity of the Promoter

Tissue samples were stained in GUS staining solution (Jefferson R. A., et al., 1987. EMBO 6:3901-3907).

This ryegrass gene promoter has high level of expression in the leaf and internodes/culm throughout the rice's growth stages, and has moderate level of expression in the root and in the spikelets (Table 2; FIG. 6).

TABLE 2

| | Qualitative GUS assay | | | | | |
|---|---|---|---|---|---|---|
| Different stages of | PRO26 | | | DCaMV35S | | |
| Histochemical GUS staining | 1103601 Staining result | 1103604 Staining result | 1103612 Staining result | 1093001 Staining result | 1093004 Staining result | Wild Type Staining result |
| Early tillering stage | | | | | | |
| Leaf | Positive | Positive | Positive | Positive | Positive | Negative |
| Active tillering stage | | | | | | |
| Leaf | Positive | Positive | Positive | Positive | Positive | Negative |
| Root | mild stain | mild stain | Positive | Positive | Positive | Negative |
| Late tillering stage | | | | | | |
| Leaf | Positive | Positive | Positive | Positive | Positive | Negative |
| Flowering stage | | | | | | |
| Leaf | Positive | Positive | Positive | Positive | Positive | Negative |
| Internode | Positive | Positive | Positive | Positive | Positive | Negative |
| Root | mild stain | mild stain | mild stain | Positive | Positive | Negative |
| Spikelet | faint stain | faint stain | faint stain | Positive | Positive | Negative |
| Maturity stage | | | | | | |
| Leaf | Positive | Positive | Positive | Positive | Positive | Negative |
| Internode | Positive | Positive | Positive | Positive | Positive | Negative |
| Root | faint stain | mild stain | mild stain | Positive | Positive | Negative |
| Spikelet | faint stain | faint stain | faint stain | Positive | Positive | Negative |

TABLE 3

| construct ID | Event ID | Activity of the extract (pmol/min/µg) |
|---|---|---|
| PRO26 | 1103601 | 2.23 |
| PRO26 | 1103604 | 3.18 |
| PRO26 | 1103612 | 79.80 |
| D35sP | 1093001 | 0.08 |
| D35sP | 1093004 | 53.73 |
| control | Nipponbare | 0.07 |

Deletion Analysis

Restriction enzymes can be used to make promoter deletions in order to test the control of gene expression by fragments of the promoter.

Shown below are three examples of such fragments with the pair of restriction enzymes and the size of the resulting promoter fragment indicated.

Promoter Fragment 1:

PRO26 del SmaI_AscI/PacI/PstI (303 bp)
(SEQ ID NO: 9)
GGGGCCGGCCGGCCGGCCACGAACGCGCCGCGCGGCCTAGAACATTCGG

TCCCCCTCTCCCGACCAGTCGCGCTCTGCCTGTCCGCAGGGAGTATTTA

TTAGCGAGCACCGGCCATTTTCCCGCGGAAGGAAACGAGCCGCGACGCT

GGTCTTGCATTCTTGTGATTACCCGCGCTGGATTCTTCCGTTTCCAAGA

GCGATTCCTCGATCGGAGCAGAGTTCCTCTGGGATAATTGCTGGTTGGT

TGCTGCTCCCGGCTACACGAAGATCCTATCGTCGCCTTCGGTTTGATTG

ATCCGTCCAACTTATGGTCCGGACCATGGATCC

Promoter Fragment 2:

PRO26 del SmaI_NcoI (361 bp)
(SEQ ID NO: 10)
CAAGAGACAAAATTGCCGGGATTCATTTCGAGTAGCGACACTTGACGAG

AACATTTTTTTGCTTTTCCAGAGAACCCACGAAAAAGGCCGGGAAGAA

AAAGGGTACAACTCAAACTTTCGTGTTCCAGGACGGTATCAGCATCGGC

GGCTCAGCCAATCACGAGCTTTGGCAAGAAATGTCGACGGAAGAAAAAT

GGCAGAAAATTTGTCGCCGTCGTACCCCCTCCCTGCTAGCCTGTCGACC

GCCGATTCGCCGTCGCGCCCACTTGCGCCGGTCGCGCGAACCTCAGCCA

CACTCTCACCAACCCAAACCCCCTGCGCTAGCTGCACCCGGCTCCGGCA

TCCAGAAGCTTCCGGCCCCATGGATCC

Promoter Fragment 3:

PRO26 del SmaI_PvuI (457 bp)
(SEQ ID NO: 11)
CAAGAGACAAAATTGCCGGGATTCATTTCGAGTAGCGACACTTGACGAG

AACATTTTTTTGCTTTTCCAGAGAACCCACGAAAAAGGCCGGGAAGAA

AAAGGGTACAACTCAAACTTTCGTGTTCCAGGACGGTATCAGCATCGGC

GGCTCAGCCAATCACGAGCTTTGGCAAGAAATGTCGACGGAAGAAAAAT

GGCAGAAAATTTGTCGCCGTCGTACCCCCTCCCTGCTAGCCTGTCGACC

GCCGATTCGCCGTCGCGCCCACTTGCGCCGGTCGCGCGAACCTCAGCCA

CACTCTCACCAACCCAAACCCCCTGCGCTAGCTGCACCCGGCTCCGGCA

TCCAGAAGCTTCCGGCCCCATCGGAGCAGAGTTCCTCTGGGATAATTGCT

GGTTGGTTGCTGCTCCCGGCTACACGAAGATCCTATCGTCGCCTTCGGT

TTGATTGATCCGTCCAACTTATGGTCCGGACCATGGATCC

Such fragments may be tested by fusion of the fragments to reporter genes such as the GUS reporter gene and histochemical staining of transformed tissue by standard methods such as those described above.

PRO26 Deletion Construct

A promoter deletion construct (PRO26 deletion construct) with the sequence corresponding to promoter fragment 2 above driving expression of the GUS gene was produced by standard techniques. In the PRO26 deletion, the SORLIP2, DRE-like promoter motif, E2F binding site motif and the transcription start sites are removed. The SORLIP1, Hexamer promoter motif, CuRE—copper response element, HSEs-like binding site motif, DPBF1&2 binding site motif, and MYB binding site are retained.

Figure 8:
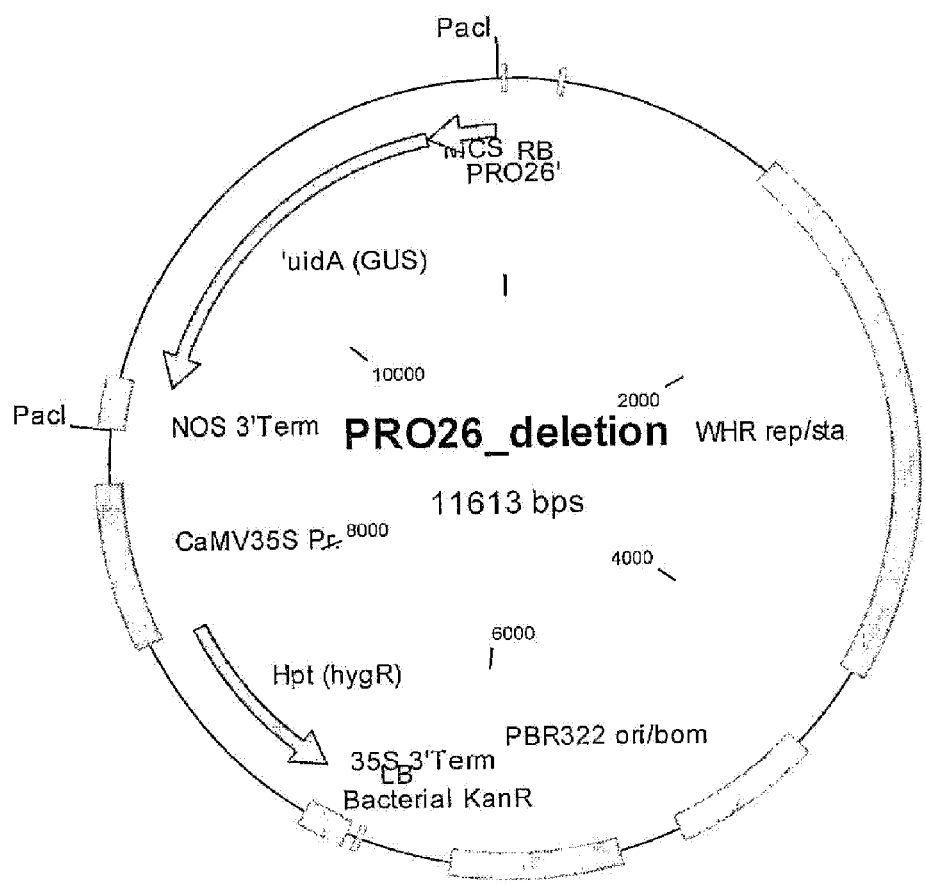
FIG. 8 shows a map of the binary vector including PRO26 deletion operably linked to the bacterial uidA gene.

The sequence of the PRO26 promoter deletion is shown in SEQ ID NO: 12. The sequence of the whole PRO26 deletion binary vector is shown in SEQ ID NO: 13. A map of the vector is shown in FIG. 8.

Table 3 below shows features of the vector.

TABLE 3

Molecule: PRO26_del_NcoI_SmaI,
11613 bps DNA Circular

| Start | End | | Name |
|---|---|---|---|
| 261 | 286 | | RB |
| 6520 | 6545 | | LB |
| 6810 | 6595 | C* | 35S 3'Term |
| 7861 | 6839 | C* | HptII (hygR) |
| 8678 | 7897 | C* | CaMV35S Pr. |
| 9179 | 8937 | C* | NOS 3'Term |
| 11211 | 9190 | C* | uidA (GUS) |
| 11577 | 11216 | C* | PRO26 deletion |

Note:
C* = Complimentary sequence

The PRO26 deletion construct was transformed into Rice as described in Example 2.

The activity of the PRO26 deletion promoter was compared to that of the full-length PRO26 promoter and the double 35S GUS promoter in respective transgenic plants, by real time PCR analysis.

Real Time PCR

RNA Extraction and mRNA Isolation

Frozen ryegrass leaf tissues harvested from plants growing in tissue culture vessels were ground independently in liquid nitrogen. Total RNA was extracted using the RNeasy Plant Mini Kit (Qiagen, Hilden, Germany) according to the manufacturers' protocol. Residual genomic DNA was removed by on-column DNAse I digestion, using the RNase-free DNase set (Qiagen), and mRNA was purified from total RNA using Dynabeads® Oligo (dT)$_{25}$ (Invitrogen Dynal AS, Oslo, Norway). The mRNA concentration and purity were determined using a Nanodrop ND-1000 spectrophotometer (Nanodrop Technologies, Wilmington, Del., USA); each mRNA sample was assayed twice and an average value determined.

First Strand cDNA Synthesis

Messenger RNA (10 ng) was reverse transcribed to produce cDNA using the Superscript III cDNA Synthesis Kit (Invitrogen, Carlsbad, Calif., US) with anchored-oligo (dT)$_{18}$ primers in total reaction volumes of 20 μl. All cDNA samples were diluted ten-fold with PCR-grade water before further use.

Real-Time qRT-PCR Conditions and Analysis

The real-time qRT-PCR were performed in 384-well plates with a LightCycler® 480 real-time PCR instrument (Roche Diagnostics, Mannheim, Germany), using the LightCycler® 480 SYBR Green I Master kit. The reaction set-up was performed on the epMotion® 5075LH automated liquid handling system (Eppendorf, Hamburg, Germany). Reactions contained 5 μl SYBR Green I Master, 2 μl PCR-grade water, 2 μl cDNA and 0.5 μl of each of the 10 μM forward and reverse gene-specific primers in a final volume of 10 μl. Each PCR reaction was performed in triplicate and no-template controls added. The reactions were incubated at 95° C. for 5 min to activate the FastStart Taq DNA polymerase, followed by 55 cycles of 95° C. for 10 sec, 55° C. for 10 sec, and 72° C. for 8 sec. The specificity of the PCR reaction was checked with a heat dissociation protocol (from 60° C. to 95° C.) following the final PCR cycle. This ensured that the resulting fluorescence originated from a single PCR product and did not represent primer-dimers formed during PCR or a non-specific product. Samples were analysed using the Abs Quant/2nd Derivative Max analysis contained in the LightCycler® 480 software. This analysis calculates the Cp value for each PCR reaction; a smaller value is indicative of abundant transcript while larger value indicates rare transcripts. The Cp values were imported into Microsoft Excel Spreadsheet and data from all transgenic plants were normalised against a constant value for the native Chlorophyll a/b binding protein gene transcript before comparing the relative abundance of uidA transcripts produced by different promoters; CaMV D35S (contro) promoter, PRO26 and PRO26 deletion. Deleting the 3' end of the PRO26 removes the promoter activity as is seen by the uidA transcript levels in PRO26 deletion::uidA transformation events.

The following primers were used:

```
Seq id: CAB Forward primer
                                    (SEQ ID NO: 14)
GTCTCGACTACCTCGGCAAC Seq id: CAB Reverse primer
                                    (SEQ ID NO: 15)
ACCGAACATGGAGAACATGG Seq id: uidA Forward primer
                                    (SEQ ID NO: 16)
GAAACTGCATCAGCCGATTA Seq id: uidA Reverse primer
                                    (SEQ ID NO: 17)
TTCACCGAAGTTCATGCCAG Seq id: hptII Forward primer
                                    (SEQ ID NO: 18)
AATACGAGGTCGCCAACATCT Seq id: hptII Reverse primer
                                    (SEQ ID NO: 19)
AGGAACCCTAATTCCCTTATCTG
```

Figure 9:
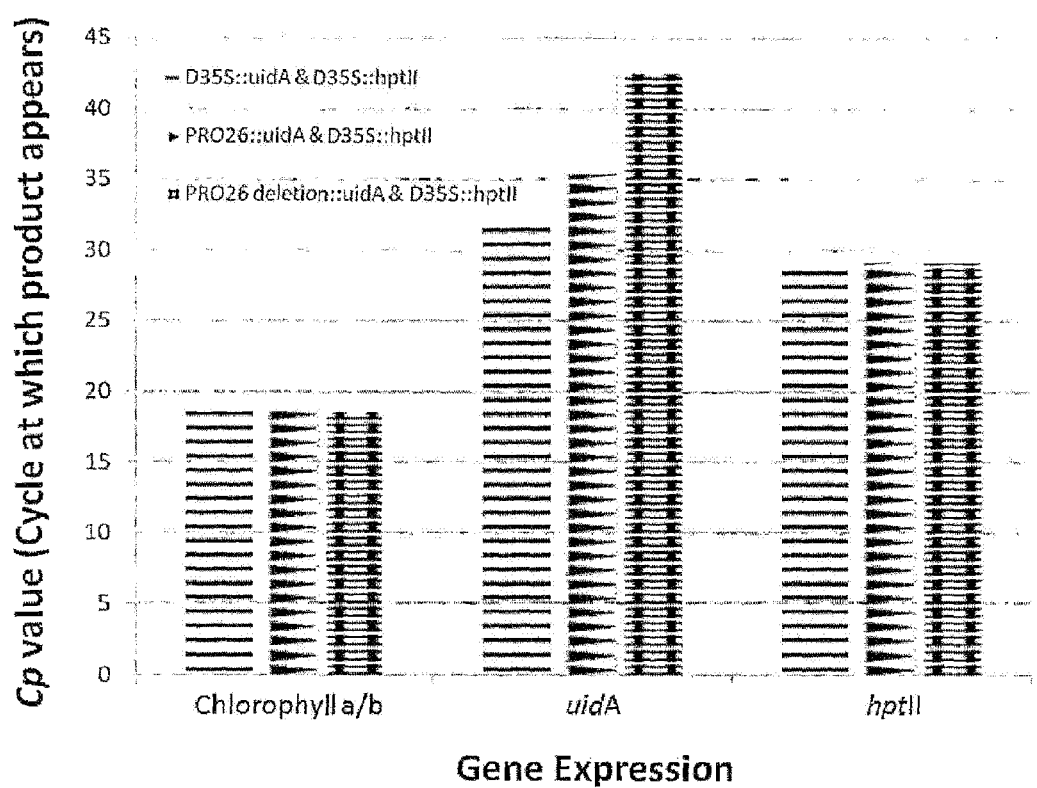
FIG. 9 shows qRT-PCR analysis of gene expression using 0.1 ng of mRNA from T0 perennial ryegrass plants transformed with different promoter-reporter (uidA) constructs. Data is normalized to constant expression of the native chlorophyll a/b binding protein gene expression across all transformation events. Data is the average of gene expression levels monitored in two D35S::uidA & D35S::hptII events; three PRO26::uidA & D35S::hptII events; and five PRO26 deletion::uidA & D35S::hptII events.

The results are presented in FIG. 9 and show that activity of the full-length PRO26 promoter is similarly but slightly less than that of the double CaMV35S promoter.

Activity of the PRO26 promoter is lost in the PRO26 deletion construct, showing that elements essential for expression of the PRO26 deletion construct are found at the 3' end of the promoter, upstream of the 3' end of the PRO26 deletion construct. Elements found in the deleted regrowth include the SORLIP2, DRE-like promoter motif, E2F binding site motif and the transcription start site.

The above Examples illustrate practice of the invention. It will be appreciated by those skilled in the art that numerous variations and modifications may be made without departing from the spirit and scope of the invention.

SUMMARY OF SEQUENCES

| SEQ ID NO: | TYPE | SPECIES | REFERENCE |
| --- | --- | --- | --- |
| 1 | Polynucleotide | *Lolium perenne* | PRO26 promoter |
| 2 | Polynucleotide | Artificial, vector | PRO26 binary construct |
| 3 | Polynucleotide | Artificial, primer | Primer |
| 4 | Polynucleotide | Artificial, primer | Primer |
| 5 | Polynucleotide | Artificial, primer | Primer |
| 6 | Polynucleotide | Artificial, primer | Primer |
| 7 | Polynucleotide | CaMV | Double 35S promoter |
| 8 | Polynucleotide | Artificial, vector | Double 35S binary construct |
| 9 | Polynucleotide | *Lolium perenne* | Promoter fragment 1 |
| 10 | Polynucleotide | *Lolium perenne* | Promoter fragment 2 |
| 11 | Polynucleotide | *Lolium perenne* | Promoter fragment 3 |
| 12 | Polynucleotide | *Lolium perenne* | PRO26 deletion |
| 13 | Polynucleotide | Artificial, vector | PRO26 binary construct |
| 14 | Polynucleotide | Artificial, primer | CAB forward primer |
| 15 | Polynucleotide | Artificial, primer | CAB reverse primer |
| 16 | Polynucleotide | Artificial, primer | uidA forward primer |
| 17 | Polynucleotide | Artificial, primer | uidA reverse primer |
| 18 | Polynucleotide | Artificial, primer | hptII forward primer |
| 19 | Polynucleotide | Artificial, primer | hptII reverse primer |

---

The invention claimed is:

1. A host cell, plant cell or plant transformed with a promoter polynucleotide, wherein the promoter polynucleotide comprises at least one of:
   a) the sequence of SEQ ID NO:1; and
   b) a sequence with at least 95% identity to the sequence of SEQ ID NO:1.

2. The host cell, plant cell or plant of claim 1, wherein the promoter polynucleotide is capable of controlling transcription of an operably linked polynucleotide in a plant.

3. The host cell, plant cell or plant of claim 1, in which the promoter polynucleotide is capable of controlling transcription of an operably linked polynucleotide sequence in at least one of leaves, internodes, roots and flowers of a plant.

4. The host cell, plant cell or plant of claim 1, in which the promoter polynucleotide is capable of driving transcription of an operably linked polynucleotide sequence more abundantly in above-ground plant parts than in the below-ground plant parts.

5. The host cell, plant cell or plant of claim 1, in which the promoter polynucleotide is capable of driving transcription of an operably linked polynucleotide sequence more abundantly in leaves and internodes than in roots and flowers of a plant.

6. The host cell, plant cell or plant of claim 1, wherein the promoter polynucleotide is part of a genetic construct.

7. The host cell, plant cell or plant of claim 6, wherein the promoter polynucleotide is operably linked to a polynucleotide sequence to be expressed.

8. A method for modifying expression of at least one polynucleotide in a plant cell or plant, the method comprising transformation of the plant cell or plant with a promoter polynucleotide of comprising at least one of:
   a) the sequence of SEQ ID NO:1; and
   b) a sequence with at least 95% identity to the sequence of SEQ ID NO:1.

9. The method of claim 8 wherein the promoter polynucleotide is part of a genetic construct.

10. A method for producing a plant cell or plant with modified expression of at least one polynucleotide, the method comprising:
   (a) transforming the plant cell or plant with a promoter polynucleotide comprising at least one of:
      i) the sequence of SEQ ID NO:1; and
      ii) a sequence with at least 95% identity to the sequence of SEQ ID NO:1;
   (b) cultivating the transgenic plant cell or plant under conditions conducive for the promoter polynucleotide to drive transcription.

11. The method of claim 10, wherein the promoter polynucleotide is part of a genetic construct.

12. The method of claim 10, wherein the promoter polynucleotide is part of a genetic construct in which the promoter polynucleotide is operably linked to a polynucleotide sequence to be expressed.

13. The method of claim 10 which results in a plant cell or plant with a modified phenotype.

14. A plant cell or plant produced by the method of claim 10.

15. A seed, propagule, progeny, part or product of a plant of claim 1.

16. The seed, propagule, progeny, part or product of claim 15, that contains a polynucleotide comprising at least one of:
   a) the sequence of SEQ ID NO:1; and
   b) a sequence with at least 95% identity to the sequence of SEQ ID NO:1.

* * * * *

UNITED STATES PATENT AND TRADEMARK OFFICE
CERTIFICATE OF CORRECTION

PATENT NO. : 8,669,108 B2  Page 1 of 1
APPLICATION NO. : 12/935952
DATED : March 11, 2014
INVENTOR(S) : Sathish Puthigae et al.

It is certified that error appears in the above-identified patent and that said Letters Patent is hereby corrected as shown below:

In the Claims

In Column 59, line 2, Claim 1, please delete "A" at the beginning of the claim and replace with --An Agrobacterium--.
In Column 59, line 2, Claim 1, please insert --, wherein said Agrobacterium host cell, said plant cell or said plant is-- between the words "plant" and "transformed".
In Column 59, line 4, Claim 1, please delete "at least one of".
In Column 59, line 5, Claim 1, please delete "and" and replace with --or--.
In Column 59, line 8, Claim 2, please insert --Agrobacterium-- between the words "The" and "host".
In Column 59, line 11, Claim 3, please insert --Agrobacterium-- between the words "The" and "host".
In Column 59, line 15, Claim 4, please insert --Agrobacterium-- between the words "The" and "host".
In Column 59, line 20, Claim 5, please insert --Agrobacterium-- between the words "The" and "host".
In Column 59, line 25, Claim 6, please insert --Agrobacterium-- between the words "The" and "host".
In Column 59, line 27, Claim 7, please insert --Agrobacterium-- between the words "The" and "host".
In Column 59, line 33, Claim 8, please delete "at least one of".
In Column 60, line 1, Claim 8, please delete "and" and replace with --or--.
In Column 60, line 10, Claim 10, please delete "at least one of".
In Column 60, line 11, Claim 10, please delete "and" and replace with --or--.
In Column 60, line 13, Claim 10, please insert the word --and-- after the words "SEQ ID NO:1;".
In Column 60, line 29, Claim 16, please delete "at least one of".
In Column 60, line 30, Claim 16, please delete "and" and replace with --or--.

Signed and Sealed this
Sixteenth Day of September, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,669,108 B2  
APPLICATION NO. : 12/935952  
DATED : March 11, 2014  
INVENTOR(S) : Puthigae et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 542 days.

Signed and Sealed this

Twenty-ninth Day of September, 2015

Michelle K. Lee
*Director of the United States Patent and Trademark Office*

SEQUENCE LISTING

```
<160> NUMBER OF SEQ ID NOS: 19

<210> SEQ ID NO 1
<211> LENGTH: 664
<212> TYPE: DNA
<213> ORGANISM: Lolium perenne

<400> SEQUENCE: 1
caagagacaa aattgccggg attcatttcg agtagcgaca cttgacgaga acattttttt      60
tgcttttcca gagaacccac gaaaaaggcc gggaagaaaa agggtacaac tcaaactttc     120
gtgttccagg acggtatcag catcggcggc tcagccaatc acgagctttg gcaagaaatg     180
tcgacggaag aaaaatggca gaaaatttgt cgccgtcgta ccccctccct gctagcctgt     240
cgaccgccga ttcgccgtcg cgcccacttg cgccggtcgc gcgaacctca gccacactct     300
caccaaccca aaccccctgc gctagctgca cccggctccg gcatccagaa gcttccggcc     360
cggggccggc cggccggcca cgaacgcgcc gcgcggccta gaacattcgg tcccctctc     420
```

| | |
|---|---|
| ccgaccagtc gcgctctgcc tgtccgcagg gagtatttat tagcgagcac cggccatttt | 480 |
| cccgcggaag gaaacgagcc gcgacgctgg tcttgcattc ttgtgattac ccgcgctgga | 540 |
| ttcttccgtt tccaagagcg attcctcgat cggagcagag ttcctctggg ataattgctg | 600 |
| gttggttgct gctcccggct acacgaagat cctatcgtcg ccttcggttt gattgatccg | 660 |
| tcca | 664 |

<210> SEQ ID NO 2
<211> LENGTH: 11931
<212> TYPE: DNA
<213> ORGANISM: Artificial
<220> FEATURE:
<223> OTHER INFORMATION: vector

<400> SEQUENCE: 2

| | |
|---|---|
| ggaattcgat atcaagcttg gcactggccg tcgttttaca acgtcgtgac tgggaaaacc | 60 |
| ctggcgttac ccaacttaat cgccttgcag cacatccccc tttcgccagc tggcgtaata | 120 |
| gcgaagaggc ccgcaccgat cgcccttccc aacagttgcg cagcctgaat ggcgaatgct | 180 |
| agagcagctt gagcttggat cagattgtcg tttcccgcct tcagtttaaa ctatcagtgt | 240 |
| ttgacaggat atattggcgg gtaaacctaa gagaaaagag cgtttattag aataacggat | 300 |
| atttaaaagg cgtgaaaag gtttatccgt tcgtccattt gtatgtgcat gccaaccaca | 360 |
| gggttcccct cgggatcaaa gtactttgat ccaacccctc cgctgctata gtgcagtcgg | 420 |
| cttctgacgt tcagtgcagc cgtcttctga aaacgacatg tcgcacaagt cctaagttac | 480 |
| gcgacaggct gccgccctgc ccttttcctg gcgttttctt gtcgcgtgtt ttagtcgcat | 540 |
| aaagtagaat acttgcgact agaaccggag acattacgcc atgaacaaga gcgccgccgc | 600 |
| tggcctgctg ggctatgccc gcgtcagcac cgacgaccag gacttgacca accaacgggc | 660 |
| cgaactgcac gcggccggct gcaccaagct gttttccgag aagatcaccg gcaccaggcg | 720 |
| cgaccgcccg gagctggcca ggatgcttga ccacctacgc cctggcgacg ttgtgacagt | 780 |
| gaccaggcta gaccgcctgg cccgcagcac ccgcgaccta ctggacattg ccgagcgcat | 840 |
| ccaggaggcc ggcgcgggcc tgcgtagcct ggcagagccg tgggccgaca ccaccacgcc | 900 |
| ggccggccgc atggtgttga ccgtgttcgc cggcattgcc gagttcgagc gttccctaat | 960 |
| catcgaccgc acccggagcg ggcgcgaggc cgccaaggcc cgaggcgtga agtttggccc | 1020 |
| ccgccctacc ctcaccccgg cacagatcgc gcacgcccgc gagctgatcg accaggaagg | 1080 |
| ccgcaccgtg aaagaggcgg ctgcactgct tggcgtgcat cgctcgaccc tgtaccgcgc | 1140 |
| acttgagcgc agcgaggaag tgacgcccac cgaggccagg cggcgcggtg ccttccgtga | 1200 |
| ggacgcattg accgaggccg acgccctggc ggccgccgag aatgaacgcc aagaggaaca | 1260 |
| agcatgaaac cgcaccagga cggccaggac gaaccgtttt tcattaccga agagatcgag | 1320 |
| gcggagatga tcgcggccgg gtacgtgttc gagccgcccg cgcacgtctc aaccgtgcgg | 1380 |
| ctgcatgaaa tcctggccgg tttgtctgat gccaagctgg cggcctggcc ggccagcttg | 1440 |
| gccgctgaag aaaccgagcg ccgccgtcta aaaaggtgat gtgtatttga gtaaaacagc | 1500 |
| ttgcgtcatg cggtcgctgc gtatatgatg cgatgagtaa ataaacaaat acgcaagggg | 1560 |
| aacgcatgaa ggttatcgct gtacttaacc agaaaggcgg gtcaggcaag acgaccatcg | 1620 |
| caacccatct agcccgcgcc ctgcaactcg ccggggccga tgttctgtta gtcgattccg | 1680 |
| atccccaggg cagtgcccgc gattgggcgg ccgtgcggga agatcaaccg ctaaccgttg | 1740 |
| tcggcatcga ccgcccgacg attgaccgcg acgtgaaggc catcggccgg cgcgacttcg | 1800 |

```
tagtgatcga cggagcgccc caggcggcgg acttggctgt gtccgcgatc aaggcagccg    1860
acttcgtgct gattccggtg cagccaagcc cttacgacat atgggccacc gccgacctgg    1920
tggagctggt taagcagcgc attgaggtca cggatggaag gctacaagcg gcctttgtcg    1980
tgtcgcgggc gatcaaaggc acgcgcatcg gcggtgaggt tgccgaggcg ctggccgggt    2040
acgagctgcc cattcttgag tcccgtatca cgcagcgcgt gagctaccca ggcactgccg    2100
ccgccggcac aaccgttctt gaatcagaac ccgagggcga cgctgcccgc gaggtccagg    2160
cgctggccgc tgaaattaaa tcaaaactca tttgagttaa tgaggtaaag agaaaatgag    2220
caaaagcaca aacacgctaa gtgccggccg tccgagcgca cgcagcagca aggctgcaac    2280
gttggccagc ctggcagaca cgccagccat gaagcgggtc aactttcagt tgccggcgga    2340
ggatcacacc aagctgaaga tgtacgcggt acgccaaggc aagaccatta ccgagctgct    2400
atctgaatac atcgcgcagc taccagagta aatgagcaaa tgaataaatg agtagatgaa    2460
ttttagcggc taaaggaggc ggcatggaaa atcaagaaca accaggcacc gacgccgtgg    2520
aatgccccat gtgtggagga acgggcggtt ggccaggcgt aagcggctgg gttgtctgcc    2580
ggccctgcaa tggcactgga accccaagcc cgaggaatc ggcgtgacgg tcgcaaacca    2640
tccggcccgg tacaaatcgg cgcggcgctg ggtgatgacc tggtggagaa gttgaaggcc    2700
gcgcaggccg cccagcggca acgcatcgag gcagaagcac gccccggtga atcgtggcaa    2760
gcggccgctg atcgaatccg caaagaatcc cggcaaccgc cggcagccgg tgcgccgtcg    2820
attaggaagc cgcccaaggg cgacgagcaa ccagattttt tcgttccgat gctctatgac    2880
gtgggcaccc gcgatagtcg cagcatcatg gacgtggccg ttttccgtct gtcgaagcgt    2940
gaccgacgag ctggcgaggt gatccgctac gagcttccag acgggcacgt agaggtttcc    3000
gcagggccgg ccggcatggc cagtgtgtgg gattacgacc tggtactgat ggcggtttcc    3060
catctaaccg aatccatgaa ccgataccgg aagggaagg gagacaagcc cggccgcgtg    3120
ttccgtccac acgttgcgga cgtactcaag ttctgccggc gagccgatgg cggaaagcag    3180
aaagacgacc tggtagaaac ctgcattcgg ttaaacacca cgcacgttgc catgcagcgt    3240
acgaagaagg ccaagaacgg ccgcctggtg acggtatccg agggtgaagc cttgattagc    3300
cgctacaaga tcgtaaagag cgaaaccggg cggccggagt acatcgagat cgagctagct    3360
gattggatgt accgcgagat cacagaaggc aagaacccgg acgtgctgac ggttcacccc    3420
gattactttt tgatcgatcc cggcatcggc cgttttctct accgcctggc acgccgcgcc    3480
gcaggcaagg cagaagccag atggttgttc aagacgatct acgaacgcag tggcagcgcc    3540
ggagagttca agaagttctg tttcaccgtg cgcaagctga tcgggtcaaa tgacctgccg    3600
gagtacgatt tgaaggagga ggcggggcag gctggcccga tcctagtcat gcgctaccgc    3660
aacctgatcg agggcgaagc atccgccggt tcctaatgta cggagcagat gctagggcaa    3720
attgccctag caggggaaaa aggtcgaaaa ggtctctttc ctgtggatag cacgtacatt    3780
gggaacccaa agccgtacat tgggaaccgg aacccgtaca ttgggaaccc aaagccgtac    3840
attgggaacc ggtcacacat gtaagtgact gatataaaag agaaaaaagg cgatttttcc    3900
gcctaaaact ctttaaaact tattaaaact cttaaaaccc gcctggcctg tgcataactg    3960
tctggccagc gcacagccga agagctgcaa aaagcgccta cccttcggtc gctgcgctcc    4020
ctacgccccg ccgcttcgcg tcggcctatc gcggccgctg gccgctcaaa aatggctggc    4080
ctacggccag gcaatctacc agggcgcgga caagccgcgc cgtcgccact cgaccgccgg    4140
cgcccacatc aaggcaccct gcctcgcgcg tttcggtgat gacggtgaaa acctctgaca    4200
```

```
catgcagctc ccggagacgg tcacagcttg tctgtaagcg gatgccggga gcagacaagc   4260
ccgtcagggc gcgtcagcgg gtgttggcgg gtgtcggggc gcagccatga cccagtcacg   4320
tagcgatagc ggagtgtata ctggcttaac tatgcggcat cagagcagat tgtactgaga   4380
gtgcaccata tgcggtgtga ataccgcac agatgcgtaa ggagaaaata ccgcatcagg    4440
cgctcttccg cttcctcgct cactgactcg ctgcgctcgg tcgttcggct gcggcgagcg   4500
gtatcagctc actcaaaggc ggtaatacgg ttatccacag aatcagggga taacgcagga   4560
aagaacatgt gagcaaaagg ccagcaaaag gccaggaacc gtaaaaaggc cgcgttgctg   4620 gcgttttttcc ataggctccg ccccctgac gagcatcaca aaaatcgacg ctcaagtcag   4680
aggtggcgaa acccgacagg actataaaga taccaggcgt ttccccctgg aagctccctc   4740
gtgcgctctc ctgttccgac cctgccgctt accggatacc tgtccgcctt tctcccttcg   4800
ggaagcgtgg cgctttctca tagctcacgc tgtaggtatc tcagttcggt gtaggtcgtt   4860
cgctccaagc tgggctgtgt gcacgaaccc cccgttcagc ccgaccgctg cgccttatcc   4920
ggtaactatc gtcttgagtc caacccggta agacacgact tatcgccact ggcagcagcc   4980
actggtaaca ggattagcag agcgaggtat gtaggcggtg ctacagagtt cttgaagtgg   5040
tggcctaact acggctacac tagaaggaca gtatttggta tctgcgctct gctgaagcca   5100
gttaccttcg gaaaaagagt tggtagctct tgatccggca aacaaaccac cgctggtagc   5160
ggtggttttt ttgtttgcaa gcagcagatt acgcgcagaa aaaaggatc tcaagaagat   5220 cctttgatct tttctacggg gtctgacgct cagtggaacg aaaactcacg ttaagggatt   5280
ttggtcatgc attctaggta ctaaaacaat tcatccagta aaatataata tttattttc    5340 tcccaatcag gcttgatccc cagtaagtca aaaaatagct cgacatactg ttcttccccg   5400
atatcctccc tgatcgaccg gacgcagaag gcaatgtcat accacttgtc cgccctgccg   5460
cttctcccaa gatcaataaa gccacttact ttgccatctt tcacaaagat gttgctgtct   5520
cccaggtcgc cgtgggaaaa gacaagttcc tcttcgggct tttccgtctt taaaaaatca   5580
tacagctcgc gcggatcttt aaatggagtg tcttcttccc agttttcgca atccacatcg   5640
gccagatcgt tattcagtaa gtaatccaat tcggctaagc ggctgtctaa gctattcgta   5700
tagggacaat ccgatatgtc gatggagtga aagagcctga tgcactccgc atacagctcg   5760
ataatctttt cagggctttg ttcatcttca tactcttccg agcaaaggac gccatcggcc   5820
tcactcatga gcagattgct ccagccatca tgccgttcaa agtgcaggac ctttggaaca   5880
ggcagctttc cttccagcca tagcatcatg tccttttccc gttccacatc ataggtggtc   5940
cctttatacc ggctgtccgt cattttttaaa tataggtttt cattttctcc caccagctta   6000
tataccttag caggagacat tccttccgta tcttttacgc agcggtattt ttcgatcagt   6060 ttttttcaatt ccggtgatat tctcatttta gccatttatt atttccttcc tcttttctac   6120
agtatttaaa gataccccaa gaagctaatt ataacaagac gaactccaat tcactgttcc   6180
ttgcattcta aaaccttaaa taccagaaaa cagcttttttc aaagttgttt tcaaagttgg   6240
cgtataacat agtatcgacg gagccgattt tgaaaccgcg gtgatcacag gcagcaacgc   6300
tctgtcatcg ttacaatcaa catgctaccc tccgcgagat catccgtgtt tcaaacccgg   6360
cagcttagtt gccgttcttc cgaatagcat cggtaacatg agcaaagtct gccgccttac   6420
aacggctctc ccgctgacgc cgtcccggac tgatgggctg cctgtatcga gtggtgattt   6480
tgtgccgagc tgccggtcgg ggagctgttg gctggctggt ggcaggatat attgtggtgt   6540
aaacaaattg acgcttagac aacttaataa cacattgcgg acgtttttaa tgtactgaat   6600
```

```
taacgccgaa ttaattcggg ggatctggat tttagtactg gattttggtt ttaggaatta    6660
gaaattttat tgatagaagt attttacaaa tacaaataca tactaagggt ttcttatatg    6720
ctcaacacat gagcgaaacc ctataggaac cctaattccc ttatctggga actactcaca    6780
cattattatg gagaaactcg agcttgtcga tcgacagatc cggtcggcat ctactctatt    6840
tctttgccct cggacgagtg ctggggcgtc ggtttccact atcggcgagt acttctacac    6900
agccatcggt ccagacggcc gcgcttctgc gggcgatttg tgtacgcccg acagtcccgg    6960
ctccggatcg gacgattgcg tcgcatcgac cctgcgccca agctgcatca tcgaaattgc    7020
cgtcaaccaa gctctgatag agttggtcaa gaccaatgcg gagcatatac gcccggagtc    7080
gtggcgatcc tgcaagctcc ggatgcctcc gctcgaagta gcgcgtctgc tgctccatac    7140
aagccaacca cggcctccag aagaagatgt tggcgacctc gtattgggaa tccccgaaca    7200
tcgcctcgct ccagtcaatg accgctgtta tgcggccatt gtccgtcagg acattgttgg    7260
agccgaaatc cgcgtgcacg aggtgccgga cttcggggca gtcctcggcc caaagcatca    7320
gctcatcgag agcctgcgcg acggacgcac tgacggtgtc gtccatcaca gtttgccagt    7380
gatacacatg gggatcagca atcgcgcata tgaaatcacg ccatgtagtg tattgaccga    7440
ttccttgcgg tccgaatggg ccgaacccgc tcgtctggct aagatcggcc gcagcgatcg    7500
catccatagc ctccgcgacc ggttgtagaa cagcgggcag ttcggtttca ggcaggtctt    7560
gcaacgtgac accctgtgca cggcgggaga tgcaataggt caggctctcg ctaaactccc    7620
caatgtcaag cacttccgga atcgggagcg cggccgatgc aaagtgccga taaacataac    7680
gatctttgta gaaaccatcg gcgcagctat ttacccgcag gacatatcca cgccctccta    7740
catcgaagct gaaagcacga gattcttcgc cctccgagag ctgcatcagg tcggagacgc    7800
tgtcgaactt ttcgatcaga aacttctcga cagacgtcgc ggtgagttca ggcttttttca    7860 tatctcattg ccccccggga tctgcgaaag ctcgagagat atagatttgt agagagagac    7920
tggtgatttc agcgtgtcct ctccaaatga aatgaacttc cttatataga ggaaggtctt    7980
gcgaaggata gtgggattgt gcgtcatccc ttacgtcagt ggagatatca catcaatcca    8040
cttgctttga agacgtggtt ggaacgtctt ctttttccac gatgctcctc gtgggtgggg    8100
gtccatcttt gggaccactg tcggcagagg catcttgaac gatagccttt cctttatcgc    8160
aatgatggca tttgtaggtg ccaccttcct tttctactgt cctttgatg aagtgacaga    8220 tagctgggca atggaatccg aggaggtttc ccgatattac cctttgttga aaagtctcaa    8280 tagcccttg gtcttctgag actgtatctt tgatattctt ggagtagacg agagtgtcgt    8340
gctccaccat gttatcacat caatccactt gctttgaaga cgtggttgga acgtcttctt    8400
tttccacgat gctcctcgtg ggtggggtc catctttggg accactgtcg gcagaggcat    8460
cttgaacgat agcctttcct ttatcgcaat gatggcattt gtaggtgcca ccttcctttt    8520
ctactgtcct tttgatgaag tgacagatag ctgggcaatg gaatccgagg aggtttcccg    8580
atattaccct ttgttgaaaa gtctcaatag ccctttggtc ttctgagact gtatctttga    8640
tattcttgga gtagacgaga gtgtcgtgct ccaccatgtt ggcaagctgc tctagccaat    8700
acgcaaaccg cctctccccg cgcgttggcc gattcattaa tgcagctggc acgacaggtt    8760
tcccgactgg aaagcgggca gtgagcgcaa cgcaattaat gtgagttagc tcactcatta    8820
ggcaccccag gctttacact ttatgcttcc ggctcgtatg ttgtgtggaa ttgtgagcgg    8880
ataacaattt cacacaggaa acagctatga ccatgattac gaattccctt aattaagatc    8940
tagtaacata gatgacaccg cgcgcgataa tttatcctag tttgcgcgct atattttgtt    9000
```

```
ttctatcgcg tattaaatgt ataattgcgg gactctaatc ataaaaaccc atctcataaa    9060
taacgtcatg cattacatgt taattattac atgcttaacg taattcaaca gaaattatat    9120
gataatcatc gcaagaccgg caacaggatt caatcttaag aaactttatt gccaaatgtg    9180
gtaccggttc attgtttgcc tccctgctgc ggttttcac  cgaagttcat gccagtccag    9240
cgttttgca  gcagaaaagc cgccgacttc ggtttgcggt cgcgagtgaa gatccctttc    9300
ttgttaccgc caacgcgcaa tatgccttgc gaggtcgcaa aatcggcgaa attccatacc    9360
tgttcaccga cgacggcgct gacgcgatca aagacgcggt gatacatatc cagccatgca    9420
cactgatact cttcactcca catgtcggtg tacattgagt gcagcccggc taacgtatcc    9480
acgccgtatt cggtgatgat aatcggctga tgcagtttct cctgccaggc cagaagttct    9540
ttttccagta ccttctctgc cgtttccaaa tcgccgcttt ggacatacca tccgtaataa    9600
cggttcaggc acagcacatc aaagagatcg ctgatggtat cggtgtgagc gtcgcagaac    9660
attacattga cgcaggtgat cggacgcgtc gggtcgagtt tacgcgttgc ttccgccagt    9720
ggcgcgaaat attcccgtgc accttgcgga cgggtatccg gttcgttggc aatactccac    9780
atcaccacgc ttgggtggtt tttgtcacgc gctatcagct ctttaatcgc ctgtaagtgc    9840
gcttgctgag tttccccgtt gactgcctct tcgctgtaca gttctttcgg cttgttgccc    9900
gcttcgaaac caatgcctaa agagaggtta aagccgacag cagcagtttc atcaatcacc    9960
acgatgccat gttcatctgc ccagtcgagc atctcttcag cgtaagggta atgcgaggta   10020
cggtaggagt tggcccccaat ccagtccatt aatgcgtggt cgtgcaccat cagcacgtta   10080
tcgaatcctt tgccacgcaa gtccgcatct tcatgacgac caaagccagt aaagtagaac   10140
ggtttgtggt taatcaggaa ctgttcgccc ttcactgcca ctgaccggat gccgacgcga   10200
agcgggtaga tatcacactc tgtctggctt ttggctgtga cgcacagttc atagagataa   10260
ccttcacccg gttgccagag gtgcggattc accacttgca aagtcccgct agtgccttgt   10320
ccagttgcaa ccacctgttg atccgcatca cgcagttcaa cgctgacatc accattggcc   10380
accacctgcc agtcaacaga cgcgtggtta cagtcttgcg cgacatgcgt caccacggtg   10440
atatcgtcca cccaggtgtt cggcgtggtg tagagcatta cgctgcgatg gattccggca   10500
tagttaaaga aatcatggaa gtaagactgc tttttcttgc cgttttcgtc ggtaatcacc   10560
attcccggcg ggatagtctg ccagttcagt tcgttgttca cacaaacggt gatacgtaca   10620
cttttcccgg caataacata cggcgtgaca tcggcttcaa atggcgtata gccgccctga   10680
tgctccatca cttcctgatt attgacccac actttgccgt aatgagtgac cgcatcgaaa   10740
cgcagcacga tacgctggcc tgcccaacct ttcggtataa agacttcgcg ctgataccag   10800
acgttgcccg cataattacg aatatctgca tcggcgaact gatcgttaaa actgcctggc   10860
acagcaattg cccggctttc ttgtaacgcg ctttcccacc aacgctgatc aattccacag   10920
ttttcgcgat ccagactgaa tgcccacagg ccgtcgagtt ttttgatttc acgggttggg   10980
gtttctacag gacggacgag tcgacggttc tgtaactatc atcatcatca tagacacacg   11040
aaataaagta atcagattat cagttaaagc tatgtaatat ttacaccata accaatcaat   11100
taaaaatag  atcagtttaa agaaagatca aagctcaaaa aaataaaaag agaaagggt    11160
cctaaccaag aaaatgaagg agaaaaacta gaaatttacc ctgtagggat ccatggtccg   11220
gaccataagt tggacggatc aatcaaaccg aaggcgacga taggatcttc gtgtagccgg   11280
gagcagcaac caaccagcaa ttatcccaga ggaactctgc tccgatcgag gaatcgctct   11340
tggaaacgga agaatccagc gcgggtaatc acaagaatgc aagaccagcg tcgcggctcg   11400
```

-continued

```
tttccttccg cggaaaatg gccggtgctc gctaataaat actccctgcg gacaggcaga    11460
gcgcgactgg tcgggagagg gggaccgaat gttctaggcc gcgcggcgcg ttcgtggccg    11520
gccggccggc cccgggccgg aagcttctgg atgccggagc cgggtgcagc tagcgcaggg    11580
ggtttgggtt ggtgagagtg tggctgaggt tcgcgcgacc ggcgcaagtg ggcgcgacgg    11640
cgaatcggcg tcgacaggc tagcaggag ggggtacgac ggcgacaaat tttctgccat      11700
ttttcttccg tcgacatttc ttgccaaagc tcgtgattgg ctgagccgcc gatgctgata    11760
ccgtcctgga acacgaaagt ttgagttgta cccttttttct tcccggcctt tttcgtgggt   11820
tctctggaaa agcaaaaaaa atgttctcgt caagtgtcgc tactcgaaat gaatcccggc    11880
aattttgtct cttgatagat ggggcgcgcc ttaattaagg cgcgccctgc a             11931
```

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3

```
gcactacatc cgttatgaag                                                   20
```

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4

```
cgaacgtctt ggtcaggaac                                                   20
```

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5

```
caagagacaa aattgccggg                                                   20
```

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6

```
tggacggatc aatcaaaccg                                                   20
```

<210> SEQ ID NO 7
<211> LENGTH: 785
<212> TYPE: DNA
<213> ORGANISM: CaMV

<400> SEQUENCE: 7

```
catggtggag cacgacactc tcgtctactc caagaatatc aaagatacag tctcagaaga     60
ccaaagggct attgagactt ttcaacaaag ggtaatatcg ggaaacctcc tcggattcca    120
ttgcccagct atctgtcact tcatcaaaag gacagtagaa aaggaaggtg gcacctacaa    180
```

```
atgccatcat tgcgataaag gaaaggctat cgttcaagat gcctctgccg acagtggtcc      240
caaagatgga cccccaccca cgaggagcat cgtggaaaaa gaagacgttc caaccacgtc      300
ttcaaagcaa gtggattgat gtgataacat ggtggagcac gacactctcg tctactccaa      360
gaatatcaaa gatacagtct cagaagacca aagggctatt gagactttc aacaaagggt       420 aatatcggga aacctcctcg gattccattg cccagctatc tgtcacttca tcaaaaggac      480
agtagaaaag gaaggtggca cctacaaatg ccatcattgc gataaaggaa aggctatcgt      540
tcaagatgcc tctgccgaca gtggtcccaa agatggaccc ccaccacga ggagcatcgt       600 ggaaaagaa gacgttccaa ccacgtcttc aaagcaagtg gattgatgtg atatctccac       660
tgacgtaagg gatgacgcac aatcccacta ccttcgcaa gaccttcctc tatataagga      720
agttcatttc atttggagag gacacgctga atcaccagt ctctctctac aaatctatct      780
ctctc                                                                  785

<210> SEQ ID NO 8
<211> LENGTH: 6129
<212> TYPE: DNA
<213> ORGANISM: Artificial
<220> FEATURE:
<223> OTHER INFORMATION: vector

<400> SEQUENCE: 8
gcgcacattt ccccgaaaag tgccacctga tgcggtgtga ataccgcac agatgcgtaa       60 ggagaaaata ccgcatcagg aaattgtaag cgttaatatt ttgttaaaat tcgcgttaaa     120 ttttttgttaa atcagctcat tttttaacca ataggccgaa atcggcaaaa tcccttataa    180
atcaaaagaa tagaccgaga tagggttgag tgttgttcca gtttggaaca agagtccact     240
attaaagaac gtggactcca acgtcaaagg gcgaaaaacc gtctatcagg gcgatggccc     300
actacgtgaa ccatcaccct aatcaagttt ttgggggtcg aggtgccgta aagcactaaa    360
tcggaaccct aaagggagcc cccgatttag agcttgacgg ggaaagccgg cgaacgtggc    420
gagaaaggaa gggaagaaag cgaaaggagc gggcgctagg gcgctggcaa gtgtagcggt    480
cacgctgcgc gtaaccacca cacccgccgc gcttaatgcg ccgctacagg gcgcgtccat    540
tcgccattca ggctgcgcaa ctgttgggaa gggcgatcgg tgcgggcctc ttcgctatta    600
cgccagctgg cgaaaggggg atgtgctgca aggcgattaa gttgggtaac gccagggttt    660
tcccagtcac gacgttgtaa aacgacggcc agtgaattgt aatacgactc actatagggc    720
gaattgggcc cgacgtcgca tgctcccggc cgccatggcg gccgcgggaa ttcgatttta    780
attaaggcgc gcccccatct ctgagcagctt gccaacatgg tggagcacga cactctcgtc    840
tactccaaga atatcaaaga tacagtctca gaagaccaaa gggctattga cttttcaa      900 caaagggtaa tatcgggaaa cctcctcgga ttccattgcc cagctatctg tcacttcatc     960
aaaaggacag tagaaaagga aggtggcacc tacaaatgcc atcattgcga taaaggaaag   1020
gctatcgttc aagatgcctc tgccgacagt ggtcccaaag atggaccccc acccacgagg   1080
agcatcgtgg aaaagaaga cgttccaacc acgtcttcaa agcaagtgga ttgatgtgaa    1140
catggtggag cacgcactc tcgtctactc caagaatatc aaagatacag tctcagaagg    1200
ccaaagggct attgagactt tcaacaaag gtaatatcg ggaaacctcc tcggattcca      1260
ttgcccagct atctgtcact tcatcaaaag gacagtagaa aaggaaggtg gcacctacaa    1320
atgccatcat tgcgataaag gaaaggctat cgttcaagat gctctgccga cagtggtccc    1380
aaagatggac ccccacccac gaggagcatc gtggaaaaag aagacgttcc aaccacgtct   1440
```

```
tcaaagcaag tggattgatg tgatatctcc actgacgtaa gggatgacgc acaatcccac   1500
tatccttcgc aagacccttc ctctatataa ggaagttcat ttcatttgga gaggacacgc   1560
tgaaatcacc agtctctctc tacaaatcta tctctctcca ttaatggtcc ggaccatgga   1620
tccctacagg gtaaatttct agttttttctc cttcatttttc ttggttagga ccctttttctc  1680 ttttttatttt tttgagcttt gatctttctt taaactgatc tatttttttaa ttgattggtt   1740 atggtgtaaa tattacatag ctttaactga taatctgatt actttatttc gtgtgtctat   1800
gatgatgatg atagttacag aaccgtcgac tcgtccgtcc tgtagaaacc ccaacccgtg   1860
aaatcaaaaa actcgacggc ctgtgggcat tcagtctgga tcgcgaaaac tgtggaattg   1920
atcagcgttg gtgggaaagc gcgttacaag aaagccgggc aattgctgtg ccaggcagtt   1980
ttaacgatca gttcgccgat gcagatattc gtaattatgc gggcaacgtc tggtatcagc   2040
gcgaagtctt ataccgaaa ggttgggcag ccagcgtat cgtgctgcgt ttcgatgcgg   2100
tcactcatta cggcaaagtg tgggtcaata atcaggaagt gatggagcat cagggcggct   2160
atacgccatt tgaagccgat gtcacgccgt atgttattgc cgggaaaagt gtacgtatca   2220
ccgtttgtgt gaacaacgaa ctgaactggc agactatccc gccggaatg gtgattaccg   2280 acgaaaacgg caagaaaaag cagtcttact tccatgattt cttaactat gccggaatcc   2340 atcgcagcgt aatgctctac accacgccga acacctgggt ggacgatatc accgtggtga   2400
cgcatgtcgc gcaagactgt aaccacgcgt ctgttgactg gcaggtggtg gccaatggtg   2460
atgtcagcgt tgaactgcgt gatgcggatc aacaggtggt gcaactgga caaggcacta   2520 gcgggacttt gcaagtggtg aatccgcacc tctggcaacc gggtgaaggt tatctctatg   2580
aactgtgcgt cacagccaaa agccagacag agtgtgatat ctacccgctt cgcgtcggca   2640
tccggtcagt ggcagtgaag ggcgaacagt tcctgattaa ccacaaaccg ttctactta   2700 ctggctttgg tcgtcatgaa gatgcggact tgcgtggcaa aggattcgat aacgtgctga   2760
tggtgcacga ccacgcatta atggactgga ttggggccaa ctcctaccgt acctcgcatt   2820
acccttacgc tgaagagatg ctcgactggg cagatgaaca tggcatcgtg gtgattgatg   2880
aaactgctgc tgtcggcttt aacctctctt taggcattgg tttcgaagcg ggcaacaagc   2940
cgaaagaact gtacagcgaa gaggcagtca acggggaaac tcagcaagcg cacttacagg   3000
cgattaaaga gctgatagcg cgtgacaaaa accacccaag cgtggtgatg tggagtattg   3060
ccaacgaacc ggatacccgt ccgcaaggtg cacgggaata tttcgcgcca ctggcggaag   3120
caacgcgtaa actcgacccg acgcgtccga tcacctgcgt caatgtaatg ttctgcgacg   3180
ctcacaccga taccatcagc gatctctttg atgtgctgtg cctgaaccgt tattacggat   3240
ggtatgtcca aagcggcgat ttggaaacgg cagagaaggt actggaaaaa gaacttctgg   3300
cctggcagga gaaactgcat cagccgatta tcatcaccga atacggcgtg gatacgttag   3360
ccgggctgca ctcaatgtac accgacatgt ggagtgaaga gtatcagtgt gcatggctgg   3420
atatgtatca ccgcgtcttt gatcgcgtca gcgccgtcgt cggtgaacag gtatggaatt   3480
tcgccgattt tgcgacctcg caaggcatat tgcgcgttgg cggtaacaag aaagggatct   3540
tcactcgcga ccgcaaaccg aagtcggcgg cttttctgct gcaaaaacgc tggactggca   3600
tgaacttcgg tgaaaaaccg cagcaggag gcaaacaatg aaccggtacc acatttggca   3660
ataaagtttc ttaagattga atcctgttgc cggtcttgcg atgattatca tataatttct   3720
gttgaattac gttaagcatg taataattaa catgtaatgc atgacgttat ttatgagatg   3780
ggtttttatg attagagtcc cgcaattata catttaatac gcgatagaaa acaaaatata   3840
```

```
gcgcgcaaac taggataaat tatcgcgcgc ggtgtcatct atgttactag atcttaatta    3900
aggcgcgcca atcactaggg tcgaccatat gggagagctc ccaacgcgtt ggatgcatag    3960
cttgagtatt ctatagtgtc acctaaatag cttggcgtaa tcatggtcat agctgtttcc    4020
tgtgtgaaat tgttatccgc tcacaattcc acacaacata cgagccggaa gcataaagtg    4080
taaagcctgg ggtgcctaat gagtgagcta actcacatta attgcgttgc gctcactgcc    4140
cgctttccag tcgggaaacc tgtcgtgcca gctgcattaa tgaatcggcc aacgcgcggg    4200
gagaggcggt ttgcgtattg ggcgctcttc cgcttcctcg ctcactgact cgctgcgctc    4260
ggtcgttcgg ctgcggcgag cggtatcagc tcactcaaag gcggtaatac ggttatccac    4320
agaatcaggg gataacgcag gaaagaacat gtgagcaaaa ggccagcaaa aggccaggaa    4380
ccgtaaaaag gccgcgttgc tggcgttttt ccataggctc cgcccccctg acgagcatca    4440
caaaaatcga cgctcaagtc agaggtggcg aaacccgaca ggactataaa gataccaggc    4500
gtttccccct ggaagctccc tcgtgcgctc tcctgttccg accctgccgc ttaccggata    4560
cctgtccgcc tttctccctt cgggaagcgt ggcgctttct catagctcac gctgtaggta    4620
tctcagttcg gtgtaggtcg ttcgctccaa gctgggctgt gtgcacgaac cccccgttca    4680
gcccgaccgc tgcgccttat ccggtaacta tcgtcttgag tccaacccgg taagacacga    4740
cttatcgcca ctggcagcag ccactggtaa caggattagc agagcgaggt atgtaggcgg    4800
tgctacagag ttcttgaagt ggtggcctaa ctacggctac actagaagaa cagtatttgg    4860
tatctgcgct ctgctgaagc cagttacctt cggaaaaaga gttggtagct cttgatccgg    4920
caaacaaacc accgctggta gcggtggttt ttttgtttgc aagcagcaga ttacgcgcag    4980
aaaaaaagga tctcaagaag atcctttgat cttttctacg gggtctgacg ctcagtggaa    5040
cgaaaactca cgttaaggga ttttggtcat gagattatca aaaaggatct tcacctagat    5100
ccttttaaat taaaaatgaa gttttaaatc aatctaaagt atatatgagt aaacttggtc    5160
tgacagttac caatgcttaa tcagtgaggc acctatctca gcgatctgtc tatttcgttc    5220
atccatagtt gcctgactcc ccgtcgtgta gataactacg atacgggagg gcttaccatc    5280
tggccccagt gctgcaatga taccgcgaga cccacgctca ccggctccag atttatcagc    5340
aataaaccag ccagccggaa gggccgagcg cagaagtggt cctgcaactt tatccgcctc    5400
catccagtct attaattgtt gccgggaagc tagagtaagt agttcgccag ttaatagttt    5460
gcgcaacgtt gttgccattg ctacaggcat cgtggtgtca cgctcgtcgt ttggtatggc    5520
ttcattcagc tccggttccc aacgatcaag gcgagttaca tgatccccca tgttgtgcaa    5580
aaaagcggtt agctccttcg gtcctccgat cgttgtcaga agtaagttgg ccgcagtgtt    5640
atcactcatg gttatggcag cactgcataa ttctcttact gtcatgccat ccgtaagatg    5700
cttttctgtg actggtgagt actcaaccaa gtcattctga atagtgta tgcggcgacc    5760 gagttgctct tgcccggcgt caatacggga taataccgcg ccacatagca gaactttaaa    5820
agtgctcatc attggaaaac gttcttcggg gcgaaaactc tcaaggatct taccgctgtt    5880
gagatccagt tcgatgtaac ccactcgtgc acccaactga tcttcagcat cttttacttt    5940
caccagcgtt tctgggtgag caaaaacagg aaggcaaaat gccgcaaaaa agggaataag    6000
ggcgacacgg aaatgttgaa tactcatact cttccttttt caatattatt gaagcattta    6060
tcagggttat tgtctcatga gcggatacat atttgaatgt atttagaaaa ataaacaaat    6120
aggggttcc                                                           6129
```

<210> SEQ ID NO 9
<211> LENGTH: 327
<212> TYPE: DNA
<213> ORGANISM: Lolium perenne

<400> SEQUENCE: 9

| | | | | | |
|---|---|---|---|---|---|
| ggggccggcc | ggccggccac | gaacgcgccg | cgcggcctag | aacattcggt | ccccctctcc | 60 |
| cgaccagtcg | cgctctgcct | gtccgcaggg | agtatttatt | agcgagcacc | ggccattttc | 120 |
| ccgcggaagg | aaacgagccg | cgacgctggt | cttgcattct | tgtgattacc | cgcgctggat | 180 |
| tcttccgttt | ccaagagcga | ttcctcgatc | ggagcagagt | tcctctggga | taattgctgg | 240 |
| ttggttgctg | ctcccggcta | cacgaagatc | ctatcgtcgc | cttcggtttg | attgatccgt | 300 |
| ccaacttatg | gtccggacca | tggatcc | | | | 327 |

<210> SEQ ID NO 10
<211> LENGTH: 370
<212> TYPE: DNA
<213> ORGANISM: Lolium perenne

<400> SEQUENCE: 10

| | | | | | |
|---|---|---|---|---|---|
| caagagacaa | aattgccggg | attcatttcg | agtagcgaca | cttgacgaga | acattttttt | 60 |
| tgcttttcca | gagaacccac | gaaaaaggcc | gggaagaaaa | agggtacaac | tcaaactttc | 120 |
| gtgttccagg | acgtatcag | catcggcggc | tcagccaatc | acgagctttg | gcaagaaatg | 180 |
| tcgacggaag | aaaaatggca | gaaaatttgt | cgccgtcgta | ccccctccct | gctagcctgt | 240 |
| cgaccgccga | ttcgccgtcg | cgcccacttg | cgccggtcgc | gcgaacctca | gccacactct | 300 |
| caccaaccca | aaccccctgc | gctagctgca | cccggctccg | gcatccagaa | gcttccggcc | 360 |
| ccatggatcc | | | | | | 370 |

<210> SEQ ID NO 11
<211> LENGTH: 481
<212> TYPE: DNA
<213> ORGANISM: Lolium perenne

<400> SEQUENCE: 11

| | | | | | |
|---|---|---|---|---|---|
| caagagacaa | aattgccggg | attcatttcg | agtagcgaca | cttgacgaga | acattttttt | 60 |
| tgcttttcca | gagaacccac | gaaaaaggcc | gggaagaaaa | agggtacaac | tcaaactttc | 120 |
| gtgttccagg | acgtatcag | catcggcggc | tcagccaatc | acgagctttg | gcaagaaatg | 180 |
| tcgacggaag | aaaaatggca | gaaaatttgt | cgccgtcgta | ccccctccct | gctagcctgt | 240 |
| cgaccgccga | ttcgccgtcg | cgcccacttg | cgccggtcgc | gcgaacctca | gccacactct | 300 |
| caccaaccca | aaccccctgc | gctagctgca | cccggctccg | gcatccagaa | gcttccggcc | 360 |
| catcggagca | gagttcctct | gggataattg | ctggttggtt | gctgctcccg | gctacacgaa | 420 |
| gatcctatcg | tcgccttcgg | tttgattgat | ccgtccaact | tatggtccgg | accatggatc | 480 |
| c | | | | | | 481 |

<210> SEQ ID NO 12
<211> LENGTH: 361
<212> TYPE: DNA
<213> ORGANISM: Lolium perenne

<400> SEQUENCE: 12

| | | | | | |
|---|---|---|---|---|---|
| caagagacaa | aattgccggg | attcatttcg | agtagcgaca | cttgacgaga | acattttttt | 60 |
| tgcttttcca | gagaacccac | gaaaaaggcc | gggaagaaaa | agggtacaac | tcaaactttc | 120 |
| gtgttccagg | acgtatcag | catcggcggc | tcagccaatc | acgagctttg | gcaagaaatg | 180 |

| | |
|---|---:|
| tcgacggaag aaaaatggca gaaaatttgt cgccgtcgta cccctccct gctagcctgt | 240 |
| cgaccgccga ttcgccgtcg cgcccacttg cgccggtcgc gcgaacctca gccacactct | 300 |
| caccaaccca acccctgc gctagctgca cccggctccg gcatccagaa gcttccggcc | 360 |
| c | 361 |

<210> SEQ ID NO 13
<211> LENGTH: 11613
<212> TYPE: DNA
<213> ORGANISM: Artificial
<220> FEATURE:
<223> OTHER INFORMATION: vector

<400> SEQUENCE: 13

| | |
|---|---:|
| ggaattcgat atcaagcttg gcactggccg tcgttttaca acgtcgtgac tgggaaaacc | 60 |
| ctggcgttac ccaacttaat cgccttgcag cacatccccc tttcgccagc tggcgtaata | 120 |
| gcgaagaggc ccgcaccgat cgcccttccc aacagttgcg cagcctgaat ggcgaatgct | 180 |
| agagcagctt gagcttggat cagattgtcg tttcccgcct tcagtttaaa ctatcagtgt | 240 |
| ttgacaggat atattggcgg gtaaacctaa gagaaaagag cgtttattag aataacggat | 300 |
| atttaaaagg gcgtgaaaag gtttatccgt tcgtccattt gtatgtgcat gccaaccaca | 360 |
| gggttcccct cgggatcaaa gtactttgat ccaaccctc gctgctata gtgcagtcgg | 420 |
| cttctgacgt tcagtgcagc cgtcttctga aaacgacatg tcgcacaagt cctaagttac | 480 |
| gcgacaggct gccgccctgc ccttttcctg gcgttttctt gtcgcgtgtt ttagtcgcat | 540 |
| aaagtagaat acttgcgact agaaccggag acattacgcc atgaacaaga gcgccgccgc | 600 |
| tggcctgctg ggctatgccc gcgtcagcac cgacgaccag gacttgacca accaacgggc | 660 |
| cgaactgcac gcggccggct gcaccaagct gttttccgag aagatcaccg gcaccaggcg | 720 |
| cgaccgcccg gagctggcca ggatgcttga ccacctacgc cctggcgacg ttgtgacagt | 780 |
| gaccaggcta gaccgcctgg cccgcagcac ccgcgaccta ctggacattg ccgagcgcat | 840 |
| ccaggaggcc ggcgcgggcc tgcgtagcct ggcagagccg tgggccgaca ccaccacgcc | 900 |
| ggccggccgc atggtgttga ccgtgttcgc cggcattgcc gagttcgagc gttccctaat | 960 |
| catcgaccgc acccggagcg ggcgcgaggc cgccaaggcc cgaggcgtga agtttggccc | 1020 |
| ccgccctacc ctcaccccgg cacagatcgc gcacgcccgc gagctgatcg accaggaagg | 1080 |
| ccgcaccgtg aaagaggcgg ctgcactgct tggcgtgcat cgctcgaccc tgtaccgcgc | 1140 |
| acttgagcgc agcgaggaag tgacgcccac cgaggccagg cggcgcggtg ccttccgtga | 1200 |
| ggacgcattg accgaggccg acgccctggc ggccgcgag aatgaacgcc aagaggaaca | 1260 |
| agcatgaaac cgcaccagga cggccaggac gaaccgtttt tcattaccga agagatcgag | 1320 |
| gcggagatga tcgcggccgg gtacgtgttc gagccgcccg cgcacgtctc aaccgtgcgg | 1380 |
| ctgcatgaaa tcctggccgg tttgtctgat gccaagctgg cggcctggcc ggccagcttg | 1440 |
| gccgctgaag aaaccgagcg ccgccgtcta aaaggtgat gtgtatttga gtaaacagc | 1500 |
| ttgcgtcatg cggtcgctgc gtatatgatg cgatgagtaa ataaacaaat acgcaagggg | 1560 |
| aacgcatgaa ggttatcgct gtacttaacc agaaaggcgg gtcaggcaag acgaccatcg | 1620 |
| caacccatct agcccgcgcc ctgcaactcg ccggggccga tgttctgtta gtcgattccg | 1680 |
| atccccaggg cagtgcccgc gattgggcgg ccgtgcggga agatcaaccg ctaaccgttg | 1740 |
| tcggcatcga ccgcccgacg attgaccgcg acgtgaaggc catcggccgg cgcgacttcg | 1800 |
| tagtgatcga cggagcgccc caggcggcgg acttggctgt gtccgcgatc aaggcagccg | 1860 |

```
acttcgtgct gattccggtg cagccaagcc cttacgacat atgggccacc gccgacctgg    1920
tggagctggt taagcagcgc attgaggtca cggatggaag gctacaagcg gcctttgtcg    1980
tgtcgcgggc gatcaaaggc acgcgcatcg gcggtgaggt tgccgaggcg ctggccgggt    2040
acgagctgcc cattcttgag tcccgtatca cgcagcgcgt gagctaccca ggcactgccg    2100
ccgccggcac aaccgttctt gaatcagaac ccgagggcga cgctgcccgc gaggtccagg    2160
cgctggccgc tgaaattaaa tcaaaactca tttgagttaa tgaggtaaag agaaaatgag    2220
caaaagcaca aacacgctaa gtgcggccg tccgagcgca cgcagcagca aggctgcaac    2280
gttggccagc ctggcagaca cgccagccat gaagcgggtc aactttcagt tgccggcgga    2340
ggatcacacc aagctgaaga tgtacgcggt acgccaaggc aagaccatta ccgagctgct    2400
atctgaatac atcgcgcagc taccagagta atgagcaaa tgaataaatg agtagatgaa    2460
ttttagcggc taaggaggc ggcatggaaa atcaagaaca accaggcacc gacgccgtgg    2520
aatgccccat gtgtggagga acgggcggtt ggccaggcgt aagcggctgg ttgtctgcc    2580 ggccctgcaa tggcactgga accccaagc ccgaggaatc ggcgtgacgg tcgcaaacca    2640
tccggcccgg tacaaatcgg cgcggcgctg ggtgatgacc tggtggagaa gttgaaggcc    2700
gcgcaggccg cccagcggca acgcatcgag gcagaagcac gccccggtga atcgtggcaa    2760
gcggccgctg atcgaatccg caaagaatcc cggcaaccgc cggcagccgg tgcgccgtcg    2820
attaggaagc cgcccaaggg cgacgagcaa ccagattttt tcgttccgat gctctatgac    2880
gtgggcaccc gcgatagtcg cagcatcatg gacgtggccg ttttccgtct gtcgaagcgt    2940
gaccgacgag ctggcgaggt gatccgctac gagcttccag acgggcacgt agaggtttcc    3000
gcagggccgg ccggcatggc cagtgtgtgg gattacgacc tggtactgat ggcggttttcc    3060 catctaaccg aatccatgaa ccgataccgg gaagggaagg gagacaagcc cggccgcgtg    3120
ttccgtccac acgttgcgga cgtactcaag ttctgccggc gagccgatgg cggaaagcag    3180
aaagacgacc tggtagaaac ctgcattcgg ttaaacacca cgcacgttgc catgcagcgt    3240
acgaagaagg ccaagaacgg ccgcctggtg acggtatccg agggtgaagc cttgattagc    3300
cgctacaaga tcgtaaagag cgaaaccggg cggccggagt acatcgagat cgagctagct    3360
gattggatgt accgcgagat cacagaaggc aagaacccgg acgtgctgac ggttcacccc    3420
gattactttt tgatcgatcc cggcatcggc cgttttctct accgcctggc acgccgcgcc    3480
gcaggcaagg cagaagccag atggttgttc aagacgatct acgaacgcag tggcagcgcc    3540
ggagagttca agaagttctg tttcaccgtg cgcaagctga tcgggtcaaa tgacctgccg    3600
gagtacgatt tgaaggagga ggcgggcag gctggcccga tcctagtcat cgcgtaccgc    3660
aacctgatcg agggcgaagc atccgccggt tcctaatgta cggagcagat gctagggcaa    3720
attgccctag caggggaaaa aggtcgaaaa ggtctctttc ctgtggatag cacgtacatt    3780
gggaacccaa agccgtacat tgggaaccgg aaccgtaca ttgggaaccc aaagccgtac    3840
attgggaacc ggtcacacat gtaagtgact gatataaaag agaaaaaagg cgattttttcc    3900 gcctaaaact ctttaaaact tattaaaact cttaaaccc gcctggcctg tgcataactg    3960
tctggccagc gcacagccga agagctgcaa aaagcgccta cccttcggtc gctgcgctcc    4020
ctacgccccg ccgcttcgcg tcggcctatc gcggccgctg gccgctcaaa aatgctggc    4080 ctacggccag gcaatctacc agggcgcgga caagccgcgc cgtcgccact cgaccgccgg    4140
cgcccacatc aaggcaccct gcctcgcgcg tttcggtgat gacggtgaaa acctctgaca    4200
catgcagctc ccggagacgg tcacagcttg tctgtaagcg gatgccggga gcagacaagc    4260
```

```
ccgtcagggc gcgtcagcgg gtgttggcgg gtgtcgggc gcagccatga cccagtcacg    4320
tagcgatagc ggagtgtata ctggcttaac tatgcggcat cagagcagat tgtactgaga    4380
gtgcaccata tgcggtgtga ataccgcac agatgcgtaa ggagaaaata ccgcatcagg    4440
cgctcttccg cttcctcgct cactgactcg ctgcgctcgg tcgttcggct gcggcgagcg    4500
gtatcagctc actcaaaggc ggtaatacgg ttatccacag aatcagggga taacgcagga    4560
aagaacatgt gagcaaaagg ccagcaaaag gccaggaacc gtaaaaaggc cgcgttgctg    4620 gcgttttttcc ataggctccg ccccctgac gagcatcaca aaaatcgacg ctcaagtcag    4680
aggtggcgaa acccgacagg actataaaga taccaggcgt ttccccctgg aagctccctc    4740
gtgcgctctc ctgttccgac cctgccgctt accggatacc tgtccgcctt ctcccttcg    4800 ggaagcgtgg cgctttctca tagctcacgc tgtaggtatc tcagttcggt gtaggtcgtt    4860
cgctccaagc tgggctgtgt gcacgaaccc ccgttcagc ccgaccgctg cgccttatcc    4920
ggtaactatc gtcttgagtc caacccggta agacacgact tatcgccact ggcagcagcc    4980
actggtaaca ggattagcag agcgaggtat gtaggcggtg ctacagagtt cttgaagtgg    5040
tggcctaact acggctacac tagaaggaca gtatttggta tctgcgctct gctgaagcca    5100
gttaccttcg gaaaaagagt tggtagctct tgatccggca acaaaccac cgctggtagc    5160 ggtggttttt tgtttgcaa gcagcagatt acgcgcagaa aaaaggatc tcaagaagat    5220 cctttgatct tttctacggg gtctgacgct cagtggaacg aaaactcacg ttaagggatt    5280
ttggtcatgc attctaggta ctaaaacaat tcatccagta aaatataata ttttattttc    5340
tcccaatcag gcttgatccc cagtaagtca aaaaatagct cgacatactg ttcttccccg    5400
atatcctccc tgatcgaccg gacgcagaag gcaatgtcat accacttgtc cgccctgccg    5460
cttctcccaa gatcaataaa gccacttact ttgccatctt tcacaaagat gttgctgtct    5520
cccaggtcgc cgtgggaaaa gacaagttcc tcttcgggct tttccgtctt taaaaaatca    5580
tacagctcgc gcggatcttt aaatggagtg tcttcttccc agttttcgca atccacatcg    5640
gccagatcgt tattcagtaa gtaatccaat tcggctaagc ggctgtctaa gctattcgta    5700
tagggacaat ccgatatgtc gatggagtga aagagcctga tgcactccgc atacagctcg    5760
ataatctttt cagggctttg ttcatcttca tactcttccg agcaaaggac gccatcggcc    5820
tcactcatga gcagattgct ccagccatca tgccgttcaa agtgcaggac ctttggaaca    5880
ggcagctttc cttccagcca tagcatcatg tccttttccc gttccacatc ataggtggtc    5940
cctttatacc ggctgtccgt cattttttaaa tataggtttt catttctcc caccagctta    6000 tataccttag caggagacat tccttccgta tcttttacgc agcggtattt ttcgatcagt    6060 ttttttcaatt ccggtgatat tctcatttta gccattatt atttccttcc tcttttctac    6120
agtatttaaa gataccccaa gaagctaatt ataacaagac gaactccaat tcactgttcc    6180
ttgcattcta aaaccttaaa taccagaaaa cagctttttc aaagttgttt tcaaagttgg    6240
cgtataacat agtatcgacg gagccgattt tgaaaccgcg gtgatcacag gcagcaacgc    6300
tctgtcatcg ttacaatcaa catgctaccc tccgcgagat catccgtgtt tcaaacccgg    6360
cagcttagtt gccgttcttc cgaatagcat cggtaacatg agcaaagtct gccgccttac    6420
aacggctctc ccgctgacgc cgtcccggac tgatgggctg cctgtatcga gtggtgattt    6480
tgtgccgagc tgccggtcgg ggagctgttg gctggctggt ggcaggatat attgtggtgt    6540
aaacaaattg acgcttagac aacttaataa cacattgcgg acgttttaa tgtactgaat    6600 taacgccgaa ttaattcggg ggatctggat tttagtactg gattttggtt ttaggaatta    6660
```

```
gaaatttttat tgatagaagt attttacaaa tacaaataca tactaagggt ttcttatatg    6720
ctcaacacat gagcgaaacc ctataggaac cctaattccc ttatctggga actactcaca    6780
cattattatg gagaaactcg agcttgtcga tcgacagatc cggtcggcat ctactctatt    6840
tctttgccct cggacgagtg ctggggcgtc ggtttccact atcggcgagt acttctacac    6900
agccatcggt ccagacggcc gcgcttctgc gggcgatttg tgtacgcccg acagtcccgg    6960
ctccggatcg gacgattgcg tcgcatcgac cctgcgccca agctgcatca tcgaaattgc    7020
cgtcaaccaa gctctgatag agttggtcaa gaccaatgcg gagcatatac gcccggagtc    7080
gtggcgatcc tgcaagctcc ggatgcctcc gctcgaagta gcgcgtctgc tgctccatac    7140
aagccaacca cggcctccag aagaagatgt tggcgacctc gtattgggaa tccccgaaca    7200
tcgcctcgct ccagtcaatg accgctgtta tgcggccatt gtccgtcagg acattgttgg    7260
agccgaaatc cgcgtgcacg aggtgccgga cttcggggca gtcctcggcc caaagcatca    7320
gctcatcgag agcctgcgcg acggacgcac tgacggtgtc gtccatcaca gtttgccagt    7380
gatacacatg gggatcagca atcgcgcata tgaaatcacg ccatgtagtg tattgaccga    7440
ttccttgcgg tccgaatggg ccgaacccgc tcgtctggct aagatcggcc gcagcgatcg    7500
catccatagc ctccgcgacc ggttgtagaa cagcgggcag ttcggtttca ggcaggtctt    7560
gcaacgtgac accctgtgca cggcgggaga tgcaataggt caggctctcg ctaaactccc    7620
caatgtcaag cacttccgga atcgggagcg cggccgatgc aaagtgccga taaacataac    7680 gatcttgta gaaccatcg gcgcagctat ttacccgcag acatatcca cgccctccta    7740 catcgaagct gaaagcacga gattcttcgc cctccgagag ctgcatcagg tcggagacgc    7800
tgtcgaactt ttcgatcaga aacttctcga cagacgtcgc ggtgagttca ggcttttttca    7860 tatctcattg ccccccccgga tctgcgaaag ctcgagagag atagatttgt agagagagac    7920
tggtgatttc agcgtgtcct ctccaaatga aatgaacttc cttatataga ggaaggtctt    7980
gcgaaggata gtgggattgt gcgtcatccc ttacgtcagt ggagatatca catcaatcca    8040
cttgctttga agacgtggtt ggaacgtctt ctttttccac gatgctcctc gtgggtgggg    8100
gtccatcttt gggaccactg tcggcagagg catcttgaac gatagccttt cctttatcgc    8160
aatgatggca tttgtaggtg ccaccttcct ttttctactgt cctttttgatg aagtgacaga    8220 tagctgggca atggaatccg aggaggtttc ccgatattac ccttttgttga aaagtctcaa    8280 tagccctttg gtcttctgag actgtatctt tgatattctt ggagtagacg agagtgtcgt    8340
gctccaccat gttatcacat caatccactt gctttgaaga cgtggttgga acgtcttctt    8400
tttccacgat gctcctcgtg ggtggggtgtc catctttggg accactgtcg gcagaggcat    8460
cttgaacgat agcctttcct ttatcgcaat gatggcattt gtaggtgcca ccttcctttt    8520
ctactgtcct tttgatgaag tgacagatag ctgggcaatg gaatccgagg aggtttcccg    8580
atattaccct ttgttgaaaa gtctcaatag cccttttggtc ttctgagact gtatctttga    8640
tattcttgga gtagacgaga gtgtcgtgct ccaccatgtt ggcaagctgc tctagccaat    8700
acgcaaaccg cctctccccg cgcgttggcc gattcattaa tgcagctggc acgacaggtt    8760
tcccgactgg aaagcgggca gtgagcgcaa cgcaattaat gtgagttagc tcactcatta    8820 ggcacccccag gctttacact ttatgcttcc ggctcgtatg ttgtgtggaa ttgtgagcgg    8880
ataacaattt cacacaggaa acagctatga ccatgattac gaattcccctt aattaagatc    8940 tagtaacata gatgacaccg cgcgcgataa tttatcctag tttgcgcgct atattttgtt    9000
ttctatcgcg tattaaatgt ataattgcgg gactctaatc ataaaaaccc atctcataaa    9060
```

```
taacgtcatg cattacatgt taattattac atgcttaacg taattcaaca gaaattatat   9120
gataatcatc gcaagaccgg caacaggatt caatcttaag aaactttatt gccaaatgtg   9180
gtaccggttc attgtttgcc tccctgctgc ggttttcac cgaagttcat gccagtccag    9240
cgttttgca gcagaaaagc cgccgacttc ggtttgcggt cgcgagtgaa gatccctttc    9300
ttgttaccgc caacgcgcaa tatgccttgc gaggtcgcaa aatcggcgaa attccatacc   9360
tgttcaccga cgacggcgct gacgcgatca aagacgcggt gatacatatc cagccatgca   9420
cactgatact cttcactcca catgtcggtg tacattgagt gcagcccggc taacgtatcc   9480
acgccgtatt cggtgatgat aatcggctga tgcagtttct cctgccaggc cagaagttct   9540
ttttccagta ccttctctgc cgtttccaaa tcgccgcttt ggacatacca tccgtaataa   9600
cggttcaggc acagcacatc aaagagatcg ctgatggtat cggtgtgagc gtcgcagaac   9660
attacattga cgcaggtgat cggacgcgtc gggtcgagtt tacgcgttgc ttccgccagt   9720
ggcgcgaaat attcccgtgc accttgcgga cgggtatccg gttcgttggc aatactccac   9780
atcaccacgc ttgggtggtt tttgtcacgc gctatcagct cttttaatcgc ctgtaagtgc   9840
gcttgctgag tttccccgtt gactgcctct tcgctgtaca gttcttttcgg cttgttgccc   9900
gcttcgaaac caatgcctaa agagaggtta aagccgacag cagcagtttc atcaatcacc   9960
acgatgccat gttcatctgc ccagtcgagc atctcttcag cgtaagggta atgcgaggta  10020
cggtaggagt tggccccaat ccagtccatt aatgcgtggt cgtgcaccat cagcacgtta  10080
tcgaatcctt tgccacgcaa gtccgcatct tcatgacgac caaagccagt aaagtagaac  10140
ggtttgtggt taatcaggaa ctgttcgccc ttcactgcca ctgaccggat gccgacgcga  10200
agcgggtaga tatcacactc tgtctggctt ttggctgtga cgcacagttc atagagataa  10260
ccttcacccg gttgccagag gtgcggattc accacttgca aagtcccgct agtgccttgt  10320
ccagttgcaa ccacctgttg atccgcatca cgcagttcaa cgctgacatc accattggcc  10380
accacctgcc agtcaacaga cgcgtggtta cagtcttgcg cgacatgcgt caccacggtg  10440
atatcgtcca cccaggtgtt cggcgtggtg tagagcatta cgctgcgatg gattccggca  10500
tagttaaaga aatcatggaa gtaagactgc ttttttcttgc cgttttcgtc ggtaatcacc  10560
attcccggcg ggatagtctg ccagttcagt tcgttgttca cacaaacggt gatacgtaca  10620
cttttcccgg caataacata cggcgtgaca tcggcttcaa atggcgtata gccgccctga  10680
tgctccatca cttcctgatt attgacccac actttgccgt aatgagtgac cgcatcgaaa  10740
cgcagcacga tacgctggcc tgcccaacct ttcggtataa agacttcgcg ctgataccag  10800
acgttgcccg cataattacg aatatctgca tcggcgaact gatcgttaaa actgcctggc  10860
acagcaattg cccggctttc ttgtaacgcg ctttcccacc aacgctgatc aattccacag  10920
ttttcgcgat ccagactgaa tgcccacagg ccgtcgagtt ttttgatttc acgggttggg  10980
gtttctacag gacggacgag tcgacggttc tgtaactatc atcatcatca tagacacacg  11040
aaataaagta atcagattat cagttaaagc tatgtaatat ttacaccata accaatcaat  11100
taaaaaatag atcagtttaa agaaagatca aagctcaaaa aaataaaaag agaaaagggt  11160
cctaaccaag aaaatgaagg agaaaaacta gaaatttacc ctgtagggat ccatggggcc  11220
ggaagcttct ggatgccgga gccgggtgca gctagcgcag ggggtttggg ttggtgagag  11280
tgtggctgag gttcgcgcga ccggcgcaag tgggcgcgac ggcgaatcgg cggtcgacag  11340
gctagcaggg aggggtacg acggcgacaa attttctgcc atttttcttc cgtcgacatt  11400
tcttgccaaa gctcgtgatt ggctgagccg ccgatgctga taccgtcctg gaacacgaaa  11460
```

```
gtttgagttg tacccttttt cttcccggcc ttttcgtgg gttctctgga aaagcaaaaa    11520
aaatgttctc gtcaagtgtc gctactcgaa atgaatcccg gcaattttgt ctcttgatag    11580
atggggcgcg ccttaattaa ggcgcgccct gca                                 11613
```

```
<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
gtctcgacta cctcggcaac                                                    20

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
accgaacatg gagaacatgg                                                    20

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
gaaactgcat cagccgatta                                                    20

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
ttcaccgaag ttcatgccag                                                    20

<210> SEQ ID NO 18
<211> LENGTH: 21
<212> TYPE: DNA
<213> ORGANISM: Artificial
<220> FEATURE:
<223> OTHER INFORMATION: primer

<400> SEQUENCE: 18
aatacgaggt cgccaacatc t                                                  21

<210> SEQ ID NO 19
<211> LENGTH: 23
<212> TYPE: DNA
<213> ORGANISM: Artificial
<220> FEATURE:
<223> OTHER INFORMATION: primer

<400> SEQUENCE: 19 aggaaccccta attcccttat ctg                                               23
```